United States Patent
Kiani et al.

(10) Patent No.: US 12,077,771 B2
(45) Date of Patent: Sep. 3, 2024

(54) UNIVERSAL PLATFORM TO ENHANCE CRISPR-BASED GENE EDITING FOR IN VIVO THERAPIES

(71) Applicant: ARIZONA BOARD OF REGENTS ON BEHALF OF ARIZONA STATE UNIVERSITY, Scottsdale, AZ (US)

(72) Inventors: Samira Kiani, Scottsdale, AZ (US); Mo Reza Ebrahimkhani, Scottsdale, AZ (US); Jennifer Chapman, Phoenix, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 18/327,373

(22) Filed: Jun. 1, 2023

(65) Prior Publication Data
US 2024/0002878 A1    Jan. 4, 2024

Related U.S. Application Data

(63) Continuation of application No. 16/626,016, filed as application No. PCT/US2018/039577 on Jun. 26, 2018, now abandoned.

(60) Provisional application No. 62/552,330, filed on Aug. 30, 2017, provisional application No. 62/524,988, filed on Jun. 26, 2017.

(51) Int. Cl.
| | | |
|---|---|---|
| C12N 15/85 | (2006.01) | |
| C12N 9/22 | (2006.01) | |
| C12N 15/11 | (2006.01) | |
| C12N 15/115 | (2010.01) | |
| C12N 15/62 | (2006.01) | |
| C12N 15/90 | (2006.01) | |

(52) U.S. Cl.
CPC ............. *C12N 15/85* (2013.01); *C12N 9/22* (2013.01); *C12N 15/11* (2013.01); *C12N 15/115* (2013.01); *C12N 15/62* (2013.01); *C12N 15/907* (2013.01); *C12N 2310/128* (2013.01); *C12N 2310/16* (2013.01); *C12N 2310/20* (2017.05); *C12N 2501/12* (2013.01); *C12N 2501/405* (2013.01); *C12N 2800/80* (2013.01)

(58) Field of Classification Search
CPC .......... C12N 15/85; C12N 9/22; C12N 15/11; C12N 15/115; C12N 15/62; C12N 15/907; C12N 2310/128; C12N 2310/20; C12N 2501/12; C12N 2501/405; C12N 2800/80; C12N 15/63; C12N 15/102
See application file for complete search history.

(56) References Cited

U.S. PATENT DOCUMENTS

| | | |
|---|---|---|
| 11,041,154 B2 | 6/2021 | Kiani et al. |
| 11,208,640 B2 | 12/2021 | Ewaisha et al. |
| 11,407,985 B2 | 8/2022 | Cong |
| 2016/0208288 A1 | 7/2016 | Liu |
| 2016/0340661 A1 | 11/2016 | Cong |
| 2021/0154326 A1 | 5/2021 | Kiani et al. |
| 2021/0155954 A1 | 5/2021 | Kiani et al. |

FOREIGN PATENT DOCUMENTS

| | | |
|---|---|---|
| WO | 2017040786 A1 | 3/2017 |
| WO | 2019005853 A2 | 1/2019 |
| WO | 2019005856 A1 | 1/2019 |
| WO | 2019017988 A1 | 1/2019 |
| WO | 2019018041 A1 | 1/2019 |
| WO | 2019237124 A1 | 12/2019 |
| WO | 2020097344 A1 | 5/2020 |

OTHER PUBLICATIONS

Altboum, Z., et al. Digital cell quantification identifies global immune cell dynamics during influenza infection. Molecular systems biology 10, 720 (2014).
Barrangou, R. et al (2016). Applications of CRISPR technologies in research and beyond. Nature Biotechnology, 34(9), 933-941. doi:10.1038/nbt.3659.
Benten, D., et al. Hepatic targeting of transplanted liver sinusoidal endothelial cells in intact mice. Hepatology 42, 140-148 (2005).
Bertolino, P., et al. Role of primary intrahepatic T-cell activation in the 'liver tolerance effect'. Immunology and cell biology 80, 84-92 (2002).
Bertolino, P., et al. Hepatocytes induce functional activation of naive CD8+ T lymphocytes but fail to promote survival. European journal of immunology 28, 221-236 (1998).
Beumer, K.J., et al. (2013). Donor DNA utilization during gene targeting with zinc-finger nucleases. G3: Genes|Genomes|Genetics, 3(4), 657-664. doi:10.1534/g3.112.005439.
Bozas, A., et al. (2009). Genetic analysis of zinc-finger nuclease-induced gene targeting in *Drosophila*. Genetics, 182(3), 641-651. doi:10.1534/genetics.109.101329.
Callery, M.P., et al. The effect of portacaval shunt on delayed-hypersensitivity responses following antigen feeding. The Journal of surgical research 46, 391-394 (1989).
Carambia, A., et al. TGF-beta-dependent induction of CD4(+)CD25 (+)Foxp3(+) Tregs by liver sinusoidal endothelial cells. Journal of hepatology 61, 594-599 (2014).

(Continued)

*Primary Examiner* — Ganapathirama Raghu
(74) *Attorney, Agent, or Firm* — Quarles & Brady, LLP

(57) ABSTRACT

Aspects of the disclosure relate to methods and synthetic regulatory systems for more efficient nuclease-mediated homology-directed repair (HDR). In particular, provided herein are methods for more efficient in vivo and in vitro HDR-based gene editing where the methods comprise introducing into a cell a synthetic regulatory system comprising Cas nuclease, guide RNAs (gRNAs) having various lengths and configured to target distinct nucleotide sequences for simultaneous transcriptional repression (or activation) and genome editing via double stranded break and use of a donor nucleic acid molecule as a template for repair.

8 Claims, 12 Drawing Sheets

Specification includes a Sequence Listing.

(56) References Cited

OTHER PUBLICATIONS

Chapman, J.E., et al. (2017). Approaches to reduce CRISPR off-target effects for safer genome editing. Applied Biosafety, 22(1), 7-13. doi: 10.1177/ 1535676017694148.
Chen, F., et al. (2017). Knockdown of FOXK1 suppresses proliferation, migration, and invasion in prostate cancer cells. Oncology Research, 25(8), 1261-1267. doi:10.3727/096504017X14871164924588.
Chew, W.L., et al. A multifunctional AAV-CRISPR-Cas9 and its host response. Nature methods 13, 868-874 (2016).
Chu, V.T. , et al. "Increasing the efficiency of homology-directed repair for CRISPR-Cas9-induced precise gene editing in mammalian cells." Nature biotechnology 33.5 (2015): 543-548.
Conlin, M.P., et al. (2017). DNA ligase IV guides end-processing choice during nonhomologous end joining. Cell Reports, 20(12), 2810-2819. doi:10.1016/j. celrep.2017.08.091.
Crispe, I.N. The liver as a lymphoid organ. Annual review of immunology 27, 147-163 (2009).
Davis, A.J. et al. (2013). DNA double strand break repair via non-homologous end-joining. Translational Cancer Research, 2(3), 130-143. doi:10.3978/j.issn. 2218-676X.2013.04.02.
Deltcheva, E., et al. (2011). CRISPR RNA maturation by trans-encoded small RNA and host factor RNase III. Nature, 471(7340), 602-607. doi:10.1038/nature09886.
Doudna, J.A. et al. (2014). The new frontier of genome engineering with CRISPR-Cas9. Science, 346(6213), 1258096-1-1258096-9. doi:10.1126/science.1258096.
Ebrahimkhani, M.R., et al. Cross-presentation of antigen by diverse subsets of murine liver cells. Hepatology 54, 1379-1387 (2011).
Evers, B., et al. (2016). CRISPR knockout screening outperforms shRNA and CRISPRi in identifying essential genes. Nature Biotechnology, 34(6), 631-633. doi: 10.1038/nbt.3536.
Fu, Y., et al. (2014). Improving CRISPR/Cas nuclease specificity using truncated guide RNAs. Nature Biotechnology, 32(3), 279-284. doi:10.1038/nbt.2808.
Gilbert, L.A., et al. (2013). CRISPR-mediated modular RNA-guided regulation of transcription in eukaryotes. Cell, 154(2), 442-451. doi:10.1016/j.cell.2013.06.044.
Glaser, A., et al. (2016). GFP to BFP conversion: A versatile assay for the quantification of CRISPR/Cas9-mediated genome editing. Molecular Therapy—Nucleic Acids, 5(7), e334. doi:10.1038/mtna.2016.48.
Graham, D.B. et al. (2015). Resources for the design of CRISPR gene editing experiments. Genome Biology, 16(1), 260-280. doi:10.1186/s13059-015-0823-x.
Groner, A.C., et al. (2010). KRAB-zinc finger proteins and KAP1 can mediate long-range transcriptional repression through heterochromatin spreading. PLoS Genetics, 6(3), e1000869. doi:10.1371/journal.pgen.1000869.
Haft, D. H., et al. "A guild of 45 CRISPR-associated (Cas) protein families and multiple CRISPR/Cas subtypes exist in prokaryotic genomes." PLoS computational biology 1.6 (2005).
Heymann, F., et al. Liver inflammation abrogates immunological tolerance induced by Kupffer cells. Hepatology 62, 279-291 (2015).
Hoffman, B.E., et al. Muscle as a target for supplementary factor IX gene transfer. Human gene therapy 18, 603-613 (2007).
Horst, A.K., et al. Modulation of liver tolerance by conventional and nonconventional antigen-presenting cells and regulatory immune cells. Cellular & molecular immunology 13, 277-292 (2016).
Hsu, P.D., et al. (2014). Development and applications of CRISPR-Cas9 for genome engineering. Cell, 57(6), 1262-1278. doi:10.1016/j.cell.2014.05. 010.
International Searching Authority, International Search Report and Written Opinion for application PCT/US2018/039577, mailed on Sep. 26, 2018.
Jinek, M., et al. (2012). A programmable dual-RNA-guided DNA endonuclease in adaptive bacterial immunity. Science, 337(6096), 816-821. doi:10.1126/science.1225829.
Kearse, M., et al. (2012). Geneious Basic: An integrated and extendable desktop software platform for the organization and analysis of sequence data. Bioinformatics, 28(12), 1647-1649. doi: 10.1093/bioinformatics/bts199.
Kiani, S., et al. Cas9 gRNA engineering for genome editing, activation and repression. Nature methods 12, 1051-1054 (2015).
Kiani, S., et al. CRISPR transcriptional repression devices and layered circuits in mammalian cells. Nature methods 11, 723-726 (2014).
Knolle, P.A. Staying local-antigen presentation in the liver. Current opinion in immunology 40, 36-42 (2016).
Li, W., et al. Role of the liver in peripheral tolerance: induction through oral antigen feeding. American journal of transplantation : official journal of the American Society of Transplantation and the American Society of Transplant Surgeons 4, 1574-1582 (2004).
Li, W., et al. New insights into mechanisms of spontaneous liver transplant tolerance: the role of Foxp3-expressing CD25+CD4+ regulatory T cells. American journal of transplantation : official journal of the American Society of Transplantation and the American Society of Transplant Surgeons 8, 1639-1651 (2008).
Li, Y., et al. (2016). PDHA1 gene knockout in prostate cancer cells results in metabolic reprogramming towards greater glutamine dependence. Oncotarget, 7(33), 53837-53852. doi:10.18632/ oncotarget. 10782.
Liang, X., et al. Rapid and highly efficient mammalian cell engineering via Cas9 protein transfection. Journal of biotechnology 208, 44-53 (2015).
Luth, S., et al. Ectopic expression of neural autoantigen in mouse liver suppresses experimental autoimmune neuroinflammation by inducing antigen-specific Tregs. The Journal of clinical investigation 118, 3403-3410 (2008).
Mali, P., et al. (2013). RNA-guided human genome engineering via Cas9. Science, 339(6121), 823-826. doi:10.1126/science.1232033.
Maruyama, T., et al. (2015). Increasing the efficiency of precise genome editing with CRISPR/Cas9 by inhibition of honhomologous end joining. Nature Biotechnology, 33(5), 538-542. doi:10.1038/nbt.3190 [Corrigendum. Nature Biotechnology 34(2): Feb. 2016, 210. doi: 10.1038/nbt0216-210c].
Maruyama, T., et al. "Increasing the efficiency of precise genome editing with CRISPR-Cas9 by inhibition of nonhomologous end joining." Nature biotechnology 33.5 (2015): 538.
Mingozzi, F. et al. Immune responses to AAV vectors: overcoming barriers to successful gene therapy. Blood 122, 23-36 (2013).
Mohar, I., et al. Isolation of Non-parenchymal Cells from the Mouse Liver. Methods Mol Biol 1325, 3-17 (2015).
Ousterout, D.G., et al. Multiplex CRISPR/Cas9-based genome editing for correction of dystrophin mutations that cause Duchenne muscular dystrophy. Nature communications 6, 6244 (2015).
Pierce, A.J., et al. (1999). XRCC3 promotes homology-directed repair of DNA damage in mammalian cells. Genes & Development, 13(20), 2633-2638. doi:10.1101/gad.13.20.2633.
Pineda, M., et al. Engineered CRISPR Systems for Next Generation Gene Therapies. ACS synthetic biology (2017).
Qi, L.S., et al. (2013). Repurposing CRISPR as an RNA-guided platform for sequence-specific control of gene expression. Cell, 152(5), 1173-1183. doi:10.1016/j.cell. 2013.02.022.
Sack, B.K., et al. Development of Gene Transfer for Induction of Antigen-specific Tolerance. Molecular therapy. Methods & clinical development 1, 14013 (2014).
Sander, J.D. et al. (2014). CRISPR/Cas systems for editing, regulating and targeting genomes. Nature Biotechnology, 32(4), 347-355. doi:10.1038/nbt.2842.
Schildberg, F.A., et al. Hepatic immune regulation by stromal cells. Current opinion in immunology 32, 1-6 (2015).
Schurich, A., et al. Dynamic regulation of CD8 T cell tolerance induction by liver sinusoidal endothelial cells. J Immunol 184, 4107-4114 (2010).
Shalem, O., et al. (2014). Genome-scale CRISPR-Cas9 knockout screening in human cells. Science, 343(6166), 84-87. doi: 10.1126/science.1247005.
Shin, J. et al., "Disabling Cas9 by an anti-CRISPR DNA mimic", Science Advances, Jul. 2017, vol. 3, No. 7, 9 pages. DOI:10.1126/sciadv.1701620.

(56) References Cited

OTHER PUBLICATIONS

Sternberg, S.H., et al. (2014). DNA interrogation by the CRISPR RNA-guided endonuclease Cas9. Nature, 507(7490), 62-67. doi:10.1038/nature13011.

Su, T., et al. (2016). A CRISPR-Cas9 assisted non-homologous end-joining strategy for one-step engineering of bacterial genome. Scientific Reports, 6(37895), 1-11. doi:10.1038/srep37895.

Sun, B., et al. Enhanced response to enzyme replacement therapy in Pompe disease after the induction of immune tolerance. American journal of human genetics 81, 1042-1049 (2007).

Swiech, L., et al. In vivo interrogation of gene function in the mammalian brain using CRISPR-Cas9. Nature biotechnology 33, 102-106 (2015).

Tanaka, M. et al. The Hepatic Lymphatic Vascular System: Structure, Function, Markers, and Lymphangiogenesis. Cellular and molecular gastroenterology and hepatology 2, 733-749 (2016).

Thomson, A.W. et al. Antigen-presenting cell function in the tolerogenic liver environment. Nature reviews. Immunology 10, 753-766 (2010).

Vartak, S. V., et al. "Inhibition of nonhomologous end joining to increase the specificity of CRISPR/Cas9 genome editing." The FEBS journal 282.22 (2015): 4289-4294.

Wang, D., et al. Adenovirus-Mediated Somatic Genome Editing of Pten by CRISPR/Cas9 in Mouse Liver in Spite of Cas9-Specific Immune Responses. Human gene therapy 26, 432-442 (2015).

Wang, D., et al. The potential of adeno-associated viral vectors for gene delivery to muscle tissue. Expert opinion on drug delivery 11, 345-364 (2014).

Wang, H., et al. One-step generation of mice carrying mutations in multiple genes by CRISPR/Cas-mediated genome engineering. Cell 153, 910-918 (2013).

Wang, J.B., et al. (2010). Targeting mitochondrial glutaminase activity inhibits oncogenic transformation. Cancer Cell, 18(3), 207-219. doi: 10.1016/j.ccr.2010.08.009.

Wiedenheft, B., et al. (2012). RNA-guided genetic silencing systems in bacteria and archaea. Nature, 482(7385), 331-338. doi:10.1038/nature 10886.

Wu, F., et al. Galactosylated LDL nanoparticles: a novel targeting delivery system to deliver antigen to macrophages and enhance antigen specific T cell responses. Molecular pharmaceutics 6, 1506-1517 (2009).

Yang, C., et al. (2009). Glioblastoma cells require glutamate dehydrogenase to survive impairments of glucose metabolism or Akt signaling. Cancer Research, 69(20), 7986-7993. doi: 10.1158/0008-5472.CAN-09-2266.

Yang, R., et al. Intestinal venous drainage through the liver is a prerequisite for oral tolerance induction. Journal of pediatric surgery 29, 1145-1148 (1994).

Yang, Y., et al. A dual AAV system enables the Cas9-mediated correction of a metabolic liver disease in newborn mice. Nature biotechnology 34, 334-338 (2016).

Yin, H., et al. Genome editing with Cas9 in adult mice corrects a disease mutation and phenotype. Nature biotechnology 32, 551-553 (2014).

Yin, H., et al. Therapeutic genome editing by combined viral and non-viral delivery of CRISPR system components in vivo. Nature biotechnology 34, 328-333 (2016).

Zalatan, J. G., et al. "Engineering complex synthetic transcriptional programs with CRISPR RNA scaffolds." Cell 160.1-2 (2015): 339-350.

Zerbino, D.R., et al. (2018). Ensembl 2018. Nucleic Acids Research, 4(46)(D1), D754-D761. doi:10.1093/nar/gkx1098.

Yeo et al., An enhanced CRIS PR repressor for targeted mammalian gene regulation. Nat. Methods., 2018, vol. 15: 611-616; published on line Jul. 16, 2018. (Year: 2018).

FIGS. 2A-2B (A) Sequence in pDRGFP targeted by gRNA

CAGCGTGTCCGGCTAGGATAACAGGGTAATACCT (SEQ ID NO:12)
GTCGCACAGGCCGATCCCTATTGTCCCATTATGGA (SEQ ID NO:13)

(B) gRNA targeting pDRGFP

CACCCGTGTCCGGCTAGGGATAAC (SEQ ID NO:14)
CCACAGGCCGATCCCTATTGCAAA (SEQ ID NO:15)

(A) pX330 gRNA insert site before digestion (B) pX330 following digestion (C) Annealed & kinased gRNA oligo targeting mutated *EGFP* in pDRGFP (D) gRNA ligated into pX330

(A) Customizable gRNA insert site before digestion

CCACCGGAGACGGGATAC[CTCTC]TGTTTA (SEQ ID NO:20)
GGTGGC[CTCTG]CCTATGGCAGAGACAAAT (SEQ ID NO:21)

(B) Customizable gRNA insert site after digestion

GTTTA
C                           T
GGTGG (C) gRNA targeting LigIV ligated into pJZC74

CCACCNNNNNNNNNNNNNNGTTTA (SEQ ID NO:22)
GGTGGNNNNNNNNNNNNNNCAAAT (SEQ ID NO:23)

UNIVERSAL PLATFORM TO ENHANCE CRISPR-BASED GENE EDITING FOR IN VIVO THERAPIES

CROSS-REFERENCE TO RELATED APPLICATIONS

This application is a continuation of U.S. application Ser. No. 16/626,016, filed Dec. 23, 2019, which represents the national stage entry of PCT International Application No. PCT/US2018/039577, filed on Jun. 26, 2018, and claims the benefit of U.S. Provisional Application Nos. 62/524,988, filed Jun. 26, 2017, and 62/552,330, filed Aug. 30, 2017, each of which is hereby incorporated by reference in its entirety for all purposes.

REFERENCE TO AN ELECTRONIC SEQUENCE LISTING

The contents of the electronic sequence listing (112624.01411.xml; Size: 44,339 bytes; and Date of Creation: May 31, 2023) is herein incorporated by reference in its entirety.

BACKGROUND

While genomic research has identified a number of genetic therapy targets that can modify the course of disease, there has been limited translation of genetic therapies into clinical use. Clustered regularly interspaced short palindromic repeats (CRISPR), a bacterial adaptive immune system, and its CRISPR-associated protein 9 (Cas9), have gained attention for the ability to target and modify DNA sequences on demand with unprecedented flexibility and precision. The precision and programmability of Cas9 is derived from its complexation with a guide-RNA (gRNA) that is complementary to a desired genomic sequence. CRISPR systems open-up widespread applications including genetic disease modeling, functional screens, and synthetic gene regulation. The plausibility of in vivo genetic engineering using CRISPR has garnered significant traction as a next generation in vivo therapeutic. There are hurdles that need to be addressed before CRISPR-based strategies are fully implemented. At present, challenges associated with gene therapy techniques include unwanted immune system reactions, infection of incorrect cells, infection caused by the transfer agent, or the possibility of genes inserting into the wrong location, which has led to insertional oncogenesis in some cases. A particular concern is very low efficiency of CRISPR-mediated correction of genetic mutation using homology-directed repair (HDR) in vivo. Such low efficiency limits the therapeutic use of CRISPR-mediated correction for most diseases. Accordingly, there remains a need in the art for methods of improving the efficiency of CRISPR-based gene editing and delivery for in vivo applications.

SUMMARY

Provided herein, in some embodiments, are methods and synthetic regulatory systems for more efficient nuclease-mediated homology-directed repair (HDR). In particular, provided herein are methods for more efficient in vivo and in vitro HDR-based gene editing where the methods comprise introducing into a cell a synthetic regulatory system comprising Cas nuclease, guide RNAs (gRNAs) having various lengths and configured to target distinct nucleotide sequences for simultaneous transcriptional repression (or activation) and genome editing via double stranded break (DSB) and repair of the DSB via HDR using a supplied donor nucleic acid molecule comprising a sequence to be inserted into the target site upon repair.

In a first aspect, provided herein is a method for introducing a specific sequence into a target site on a target double-stranded nucleic acid in a cell, where the method comprises or consists essentially of (a) introducing into the cell or expressing within the cell a synthetic regulatory system comprising (i) a nucleotide sequence encoding a multifunctional Cas nuclease; (ii) at least one truncated guide RNA (gRNA) of 15 or less nucleotides (nt) in length complementary to at least a portion of a nucleotide sequence encoding a non-homologous end joining (NHEJ)-associated enzyme, whereby binding of the at least one truncated gRNA to the Cas nuclease directs the Cas nuclease to the nucleotide sequence encoding a NHEJ-associated enzyme; (iii) at least one gRNA of 16 or greater nt in length that binds to or near the target site of the target double-stranded nucleic acid; (iv) a donor nucleic acid molecule comprising the specific sequence to be inserted into the target site; wherein the nucleotide sequence encoding the Cas nuclease, the at least one truncated gRNA, and the at least one gRNA of 16 or greater nt comprise a single amplicon; and (b) inducing a double stranded break (DSB) at the target site, under conditions sufficient for the donor nucleic acid molecule to bind to the DSB and the DSB to be repaired, thereby introducing the specific sequence into the target site. The rate of homology-directed repair (HDR) compared with non-homologous end joining (NHEJ) can be increased. The multifunctional Cas nuclease can be expressed as a fusion protein comprising a transcriptional activation or repression domain. The multifunctional Cas nuclease can be fused to a transcriptional repression domain and the truncated gRNA comprises an RNA aptamer for aptamer-mediated recruitment of the Cas nuclease. The repression domain can be KRAB-MecP2, MS2-KRAB-MecP2, and Com-KRAB. The NHEJ-associated enzyme can be selected from the group consisting of XRCC4, XRCC5 (KU80), XRCC6 (KU70), and DNA ligase IV. The system can comprise four gRNAs of 15 nt or less in length, wherein each of the four gRNAs is complementary to at least a portion of a nucleotide sequence encoding a different NEHJ enzyme selected from the group consisting of XRCC4, XRCC5 (KU80), XRCC6 (KU70), and DNA ligase IV. The amplicon can further comprise a truncated activating gRNA complementary to at least a portion of a nucleotide sequence encoding cell cycle progression factor, where the truncated activating gRNA further comprises a MS2 aptamer whereby binding of the truncated activating gRNA to the nucleotide sequence recruits the Cas nuclease for transcriptional activation. The at least one cell cycle progression factor can be selected from the group consisting of hepatocyte growth factor (HGF), Cyclin A1, Cyclin A2, Cyclin B1, Cyclin E1, skp2, CtIP, cyclin dependent kinase 2 (CDK2), and Geminin (GMNN). The truncated activating gRNA can further comprise a ligand-responsive riboswitch. The ligand-responsive riboswitch can be a tetracycline riboswitch or theophylline riboswitch.

In another aspect, provided herein is a method for efficient Homology-Directed repair (HDR)-based gene editing, where the method comprises or consists essentially of introducing into a cell a synthetic regulatory system comprising (a) at least one truncated guide RNA (gRNA) of 15 or less nucleotides (nt) in length complementary to at least a portion of a nucleotide sequence encoding a non-homologous end joining (NHEJ) enzyme; (b) at least one gRNA of 16 or greater nt in length that is complementary to at least a portion of a gene targeted for genetic editing; (c) one or more RNA aptamers, where the at least one truncated gRNA and at least one gRNA, and the one or more aptamers comprise a single amplicon, and where the cell expresses a multifunctional Cas nuclease. The amplicon can further comprise a repression domain selected from the group consisting of KRAB-MecP2, MS2-KRAB-MecP2, and Com-KRAB.

BRIEF DESCRIPTION OF THE DRAWINGS

FIGS. 2A-2B illustrate an embodiment of a gRNA targeting mutated EGFP in pDRGFP (Addgene plasmid #26475). (A) Sequence in pDRGFP targeted by gRNA. The sequence shown here is the mutated portion of the EGFP gene in pDRGFP, which disrupts its expression. The I-SceI recognition sequence (gray shaded box) inactivates expression of the EGFP gene. Arrows (▲▼) indicate I-SceI cut sites. When Cas9 recognizes the PAM site (NGG; green underline) and the gRNA binds to the target sequence (blue underline), Cas9 induces a DSB (dashed line). (B) gRNA targeting pDRGFP. A 20-bp gRNA (blue underline) complementary to the target sequence in pDRGFP was designed to include overhangs (red underline) complementary to the overhangs in digested pX330 (Addgene plasmid #42230) and an extra guanine nucleotide (pink shaded box) to promote optimal expression by the hU6 promoter expressing the gRNA in pX330.

(FIG. 5A) gBlock before digestion. A 550-bp gBlock included restriction enzyme recognition sequences for XbaI and BamHI (gray shaded boxes) and a small excess of base pairs ($N_{30}$) on its ends. Restriction enzyme cut sites are indicated by arrows (▲▼). (FIG. 5B) gBlock after digestion. After digestion of the gBlock with XbaI and BamHI-HF, overhangs remain (pink underline). (FIG. 5C) Linearized pJZC74. The overhangs in linearized pJZC74 (red underline) are complementary to the overhangs in the gBlock. (FIG. 5D) gBlock inserted into pJZC74. The gBlock containing the customizable gRNA insert site was inserted into pJZC74 using the NEB Quick Ligation™ Kit.

FIG. 10A shows FACS results at 50 ng of pJZC74 with gRNA. Significant GFP was present for all gRNAs as compared to pDRGFP alone. gRNA-10 showed the highest geometric mean of $GFP^+$ cells at 50 ng of pJZC74. FIG. 10B shows FACS results at 100 ng of pJZC74 with gRNA. gRNA-9 showed the highest geometric mean of $GFP^+$ cells at 100 ng of pJZC74.

DETAILED DESCRIPTION

Figure 1:
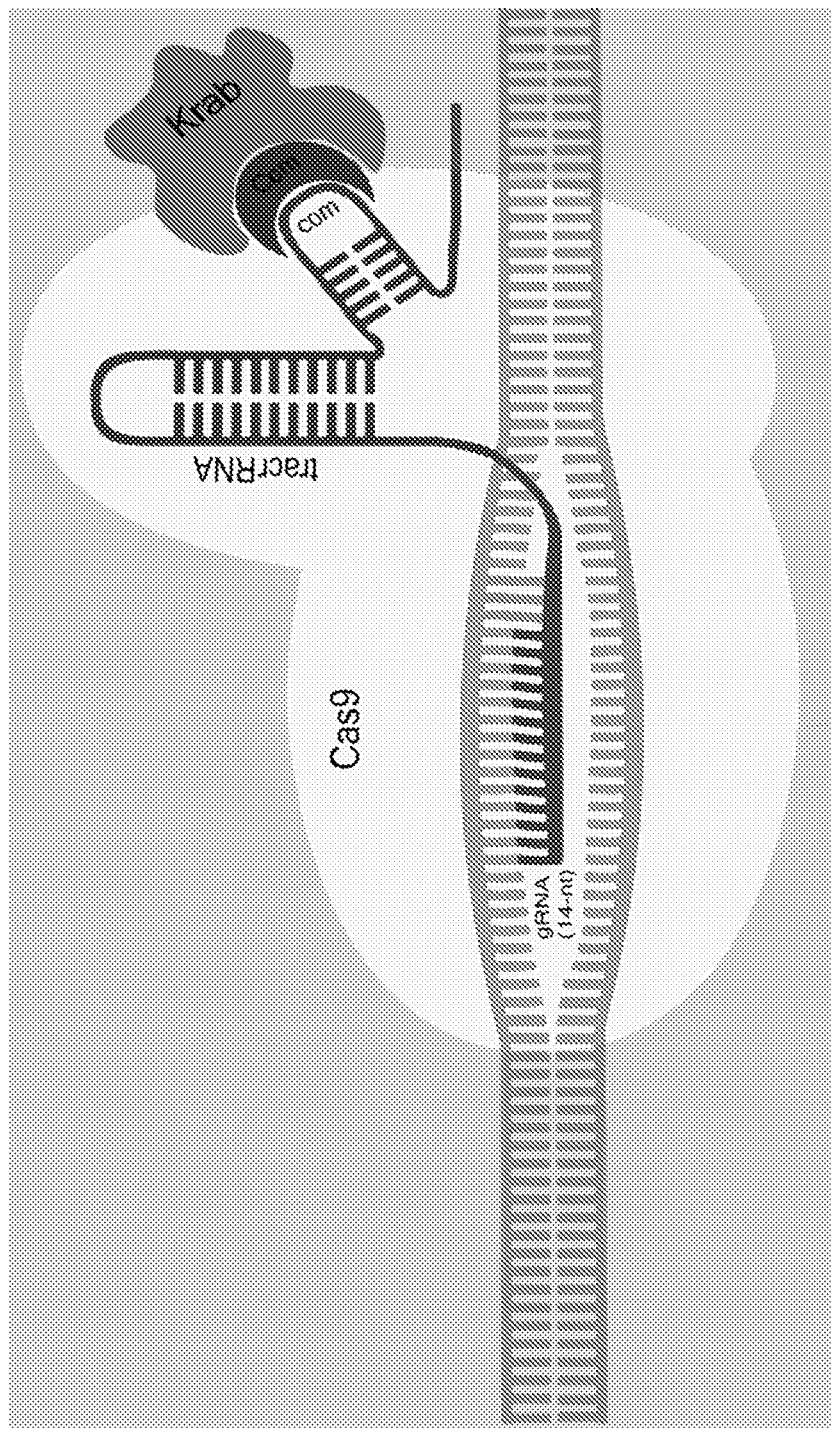
FIG. 1 illustrates extension of vector pJZC74's (Addgene plasmid #62342) gRNA to include a com protein recruitment domain that recruits the Com-KRAB fusion protein. With this extension, KRAB facilitates repression of the gene targeted by pJZC74's gRNA. Illustrated here is one embodiment in which a 14-nt gRNA was used in complex with Cas9 to target the gene of interest for repression without inducing a DSB.

All publications, including but not limited to patents and patent applications, cited in this specification are herein incorporated by reference as though set forth in their entirety in the present application.

The systems and methods provided herein are based at least in part on the inventors' development of a multifunctional platform for more efficient in vivo and in vitro clustered regularly interspaced short palindromic repeat (CRISPR)-based gene editing. By truncating the 5' end of the gRNA and decreasing its target complementarity from 20 nt to 14 nt, the inventors demonstrated that it is possible to achieve simultaneous gene disruption and modulation by a single multifunctional Cas9 complex (where Cas9 nuclease activity is modulated to simultaneously activate and mutate multiple genes in human cells) while maintaining its RNA/DNA binding capacity. The methods and systems provided herein further exploit such guide RNAs of various lengths to simultaneously repress expression of enzymes associated with or required for non-homologous end-joining (NHEJ), or activate expression of other genes, while retaining the RNA/DNA binding and gene editing capacity of a multifunctional Cas nuclease for CRISPR-mediated homology-directed repair (HDR) at a target site. In this manner, the embodiments described herein provide a universal platform or tool kit for more efficient therapeutic genome editing by CRISPR.

Other advantages of the methods and systems provided herein include, without limitation, fewer regulatory hurdles and safety issues for clinical applications of the technology. In particular, the methods involve a "CRISPR only" approach rather than use of CRISPR with shRNA or small molecules which require separate regulatory scrutiny for use with human subjects. Moreover, the genetic circuits described herein have a small enough payload for delivery using DNA viruses (e.g., adeno-associated virus (AAV)) which are commonly used viral delivery systems in clinical trials. As described herein, the methods can employ Cas nucleases derived from *Streptococcus pyogenes* (SP) or *Staphylococcus aureus* (SA)-CRISPR platforms in order to limit payload size for DNA virus delivery. In addition, the methods and systems provide a platform which can be used with Cas9-GFP transgenic mice to rapidly screen for effective homology-directed repair for in vivo uses in various tissues and organs using screening methods known in the art. See for example, Glaser et al. 2016, "GFP to BFP conversion: A versatile assay for the quantification of CRISPR/Cas9-mediated genome editing," Mol. Ther. Nucleic Acid, 5 (7):e334.

It will be understood that, although the strategies described herein for increasing the efficiency of homology-directed repair and/or reducing the efficiency of NHEJ-mediated repair use CRISPR/Cas-based RNA-guided DNA endonucleases for gene editing, many of these strategies can additionally or alternatively employ other programmable endonucleases such as zinc finger nucleases (ZFNs) and transcription activator-like effector nucleases (TALENs).

Accordingly, in a first aspect, provided herein is a method for more efficient nuclease-mediated HDR in vivo and in vitro. In particular, the method comprises introducing into a cell a synthetic regulatory system comprising a multifunctional Cas nuclease and guide RNAs (gRNAs) having various lengths and configured to target distinct nucleotide sequences for simultaneous transcriptional repression (or activation) and genome editing via a double stranded break (DSB) and repair using a donor nucleic acid molecule. The donor nucleic acid molecule comprises the specific sequence to be inserted into the target site after being of the donor nucleic acid molecule to the DSB and repair using HDR. As used herein, the term "HDR", or homology-directed repair, refers to the process of repairing DNA damage using a homologous nucleic acid (e.g., a sister chromatid or an exogenous nucleic acid). In a normal cell, HDR typically involves a series of steps such as recognition of a double stranded break, stabilization of the break, resection, stabilization of single stranded DNA, formation of a DNA crossover intermediate, resolution of the crossover intermediate, and ligation.

In certain embodiments, the method comprises (a) introducing into the cell or expressing within the cell a synthetic regulatory system comprising (i) a nucleotide sequence encoding a multifunctional Cas nuclease; (ii) at least one truncated guide RNA (gRNA) of 15 or less nucleotides (nt) in length complementary to at least a portion of a nucleotide sequence encoding a non-homologous end joining (NHEJ)-associated enzyme, whereby binding of the at least one truncated gRNA to the Cas nuclease directs the Cas nuclease to the nucleotide sequence encoding a NHEJ-associated sequence for steric hindrance mediated repression; (iii) at least one gRNA of 16 or greater nt in length that binds to or near the target site of the target nucleic acid; (iv) a donor nucleic acid molecule comprising the specific sequence to be inserted into the target nucleic acid; wherein the nucleotide sequence encoding the Cas nuclease, the at least one truncated gRNA, and the at least one gRNA of 16 or greater nt comprise a single amplicon; and (b) inducing a double stranded break (DSB) at the target site, under conditions sufficient for the donor nucleic acid molecule to bind to the DSB and the DSB to be repaired, thereby introducing the specific sequence into the target site.

"Cas9 molecule" or "Cas9 polypeptide", as used herein, refers to a polypeptide that can bind (1) a PAM (a protospacer adjacent motif) in a nucleic acid, and (2) a guide RNA (gRNA) molecule. In an embodiment, in concert with the gRNA molecule, a Cas9 molecule or Cas9 polypeptide can localize to a site which comprises a target domain. Cas9 may be a nuclease (an enzyme that cleaves both strands of a double-stranded nucleic acid), a nickase (an enzyme that cleaves one strand of a double-stranded nucleic acid), or an enzymatically inactive (or dead) molecule. In some cases, the Cas9 molecule is an altered, engineered, or modified Cas9 molecule. As used herein, the terms altered, engineered, or modified refers merely to a difference from a reference or naturally occurring sequence, and impose no specific process or origin limitations.

"Domain", as used herein, is used to describe segments of a protein or nucleic acid. Unless otherwise indicated, a domain is not required to have any specific functional property.

In some cases, the truncated guide RNAs (gRNAs) having a length of 15 or fewer (e.g., a 15-nt gRNA, a 14-nt gRNA, a 13-nt gRNA, a 12-nt gRNA, a 11-nt gRNA, a 10-nt gRNA, etc.) nucleotides is a 14-nt gRNA configured to target and repress nucleotide sequences encoding one or more enzymes required for or associated with NHEJ (e.g., LigIV, XRCC4, XRCC5 (KU80), and XRCC6 (KU70)). In some cases, the regulatory system further comprises a gRNA having a length of 16 or more nucleotides (e.g., a 16-nt gRNA, a 17-nt gRNA, a 18-nt gRNA, a 19-nt gRNA, a 20-nt gRNA, a 21-nt gRNA, etc.) configured to target a gene of interest for double stranded break and repair of the cut site using a donor nucleic acid molecule comprising a sequence to be inserted into the target site. In certain embodiments, the multiple truncated gRNAs (e.g., two or more 14 nt gRNAs) are employed to target and repress nucleotide sequences encoding two or more NHEJ enzymes such as DNA ligase IV (LigIV), XRCC4, XRCC5 (KU80), and XRCC6 (KU70). In some cases, the method employs at least four truncated gRNAs, where each of the four gRNAs is complementary to at least a portion of a nucleotide sequence encoding a different NEHJ enzyme selected from the group consisting of DNA ligase IV (LigIV), XRCC4, XRCC5 (KU80), and XRCC6 (KU70).

In some cases, the Cas nuclease is recruited to the target site for DSB through fusion or non-covalent binding to an RNA sequence or structure (e.g., an RNA aptamer) appending to a gRNA. For example, an RNA-binding domain such as MS2 or Com can be used as an RNA aptamer.

In some embodiments, Cas nuclease is encoded from an engineered nucleic acid. For example, in certain embodiments, transcriptional modifiers are fused to Cas nuclease to enable site-specific transcriptional modifications. Various strategies can be used to engineer such fusion molecules. In some cases, transcriptional modulators are directly fused to the Cas nuclease protein. In other cases, the modulator is fused to another RNA binding protein such as MS2 bacteriophage coat protein or Com in order to recruit the modulator to the Cas/gRNA/DNA complex.

In some cases, the multifunctional Cas nuclease is expressed as a fusion protein comprising a transcriptional activation or repression domain. In other cases, repression is achieved without the use of any repression domain but, rather, through Cas nuclease-mediated steric hindrance. As used herein, "steric hindrance" or "steric interference" refers to the restriction or prevention of the binding or interaction of one molecular entity (e.g., a protein or a protein fragment) with another molecular entity (e.g., a nucleic acid or a protein). The gRNA can comprise an aptamer sequence (e.g., MeCP2 and Com) fused to a repression domain such as, for example, a Kruppel associated box (KRAB) domain. Other repression domains include, without limitation, a methyl-CpG (mCpG) binding domain (e.g., binding domain for MeCP2), KRAB-MeCP2 and Com-KRAB.

Expression of some or all of the gRNAs can be under the control of a RNA polymerase type III promoter or RNA polymerase type II promoter such as, for example, HI, U6 or 7SK promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer), the SV40 promoter, the dihydrofolate reductase promoter, the β-actin promoter, the phosphoglycerol kinase (PGK) promoter, and the EF1α promoter. A promoter, generally, is a region of nucleic acid that initiates transcription of a nucleic acid encoding a product. A promoter may be located upstream (e.g., 0 bp to −100 bp, −30 bp, −75 bp, or −90 bp) from the transcriptional start site of a nucleic acid encoding a product, or a transcription start site may be located within a promoter. A promoter may have a length of 100-1000 nucleotide base pairs, or 50-2000 nucleotide base pairs. In some embodiments, promoters have a length of at least 2 kilobases (e.g., 2-5 kb, 2-4 kb, or 2-3 kb). In certain embodiments, gRNA expression from RNA pol II promoters can be modulated using Csy4 endoribonuclease-mediated cleavage. In some cases, multiple gRNAs are placed in tandem from a single coding region processed by Csy4.

In some cases, synthetic promoters on the circuit are replaced with a cell type specific promoter. For example, a synthetic RNA Pol II or Pol III promoter can be swapped with a cell type- or context-specific promoter and interfaced with intracellular signaling, enabling multistep sensing and modulation of cellular behavior. In some cases, a transcriptional repression cascade comprises two, three, or four interconnected CRISPR transcriptional repression circuits (NAND logic gates).

In some cases, the methods described herein can employ truncated gRNAs configured to target critical components of a HDR DNA repair pathway for transcriptional activation. For example, truncated gRNAs (e.g., 14-nt gRNAs) can be configured to bind at or near a nucleic acid sequence encoding a critical HDR component. In some cases, transcriptional activation domains (e.g., VP64, VP16, p65) are fused to or otherwise used in connection with the Cas nuclease and specific guide RNAs.

In a further aspect, provided herein is a "CRISPR trilogy" platform in which another layer is added to the CRISPR duology platform described herein. Specifically, the CRISPR trilogy platform comprises (i) a 20-nt gRNA and a donor template-mediated HDR; (ii) a 14-nt gRNA in complex with Cas9 for steric hindrance mediated repression of NHEJ enzymes; and (iii) Cas9-gRNA mediated activation of cell cycle genes to induce cellular proliferation. In this strategy, step (iii) comprises using another 14-nt gRNA carrying an MS2 aptamer to mediate activation of factors involved in cell cycle progression (e.g., HGF, Cyclin E1 or skp2), all within a single AAV vector. In some cases, it will be advantageous to include a riboswitch, such as a tetracycline riboswitch or theophylline riboswitch, in the 14-nt activating gRNA.

In certain embodiments, methods employing the CRISPR trilogy platform are performed as described above, but the synthetic regulatory system amplicon further comprises a truncated activating gRNA (e.g., a 14-nt gRNA) complementary to at least a portion of a nucleotide sequence encoding cell cycle progression factor, wherein the truncated activating gRNA further comprises a MS2 aptamer. Binding of such as truncated activating gRNA to the Cas nuclease directs the Cas nuclease to the nucleotide sequence for transcriptional activation of the cell cycle progression factor. Cell cycle progression factors suitable for the CRISPR trilogy platform include, without limitation, hepatocyte growth factor (HGF), Cyclin A1, Cyclin A2, Cyclin B1, Cyclin E1, skp2, CtIP (also known as RBBP8), cyclin dependent kinase 2 (CDK2), and Geminin (GMNN, a DNA replication inhibitor).

CRISPR systems belong to different classes, with different repeat patterns, sets of genes, and species ranges. A CRISPR enzyme is typically a type I or III CRISPR enzyme. The CRISPR system is derived advantageously from a type II CRISPR system. The type II CRISPR enzyme may be any Cas enzyme. The terms "Cas" and "CRISPR-associated Cas" are used interchangeably herein. The Cas enzyme can be any naturally-occurring nuclease as well as any chimeras, mutants, homologs, or orthologs. In some embodiments, one or more elements of a CRISPR system is derived from a particular organism comprising an endogenous CRISPR system, such as *Streptococcus pyogenes* (SP) CRISPR systems or *Staphylococcus aureus* (SA) CRISPR systems. The CRISPR system is a type II CRISPR system and the Cas enzyme is Cas9 or a catalytically inactive Cas9 (dCas9). Other non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. A comprehensive review of the Cas protein family is presented in Haft et al. (2005) Computational Biology, *PLoS Comput. Biol.* 1:e60. At least 41 CRISPR-associated (Cas) gene families have been described to date.

It will be understood that the CRISPR-Cas system as described herein is non-naturally occurring in a cell, i.e. engineered or exogenous to the cell. The CRISPR-Cas system as referred to herein has been introduced in a cell. Methods for introducing the CRISPR-Cas system in a cell are known in the art, and are further described herein elsewhere. The cell comprising the CRISPR-Cas system, or having the CRISPR-Cas system introduced, according to the invention comprises or is capable of expressing the individual components of the CRISPR-Cas system to establish a functional CRISPR complex, capable of modifying (such as cleaving) a target DNA sequence. Accordingly, as referred to herein, the cell comprising the CRISPR-Cas system can be a cell comprising the individual components of the CRISPR-Cas system to establish a functional CRISPR complex, capable of modifying (such as cleaving) a target DNA sequence. Alternatively, as referred to herein, and preferably, the cell comprising the CRISPR-Cas system can be a cell comprising one or more nucleic acid molecules encoding the individual components of the CRISPR-Cas system, which can be expressed in the cell to establish a functional CRISPR complex, capable of modifying (such as cleaving) a target DNA sequence.

Components of any of the synthetic regulatory circuits described herein are preferably provided in a single amplicon. In some cases, however, the components may be in the form of two or more polynucleotide sequences. The synthetic regulatory circuit can be an engineered polynucleotide. As used herein, the terms "engineered nucleic acid" and "engineered polynucleotide" are used interchangeably and refer to a nucleic acid that has been designed and made using known in vitro techniques in the art. In some embodiments, an engineered polynucleotide, also referred to as a circuit herein, is a nucleic acid that is not isolated from the genome of an organism. In some embodiments, the engineered polynucleotide is introduced to a cell, plurality of cells, an organ or an organism to perform diverse functions (e.g., differentiation of cells, as sensors within cells, program a cell to act as a sensor, and delivery of selective cell-based therapies).

In some cases, components of any of the synthetic regulatory circuits described herein are provided in a single amplicon that is packaged in a delivery vector for introduction into a cell (e.g., a mammalian cell). Any appropriate delivery vector can be used with the systems and methods described herein. For example, delivery vectors include exosomes, viruses (viral vectors), and viral particles. Preferably, the delivery vector is a viral vector, such as a lenti- or baculo- or preferably adeno-viral/adeno-associated viral (AAV) vectors, but other means of delivery are known (such as exosomes, yeast systems, microvesicles, gene guns/means of attaching vectors to gold nanoparticles) and are provided. For example, an amplicon comprising circuit components as described herein can be delivered/introduced into a cell via liposomes, nanoparticles, exosomes, microvesicles, or a gene-gun. In certain preferred embodiments, the circuit components are packaged in an amplicon for delivery to a cell in one or more viral delivery vectors. Suitable viral delivery vectors include, without limitation, adeno-viral/adeno-associated viral (AAV) vectors, lentiviral vectors, and Herpes Simplex Virus 1 (HSV-1) vectors.

Preferably, a single viral vector (e.g., an AAV vector) is used to achieve transfection of all synthetic genetic components (e.g., a truncated (14-nt) gRNA, 20 nt gRNA, and multifunctional Cas9 nuclease or a catalytically mutant Cas9 nuclease). In some embodiments, a synthetic regulatory circuit as described herein may be introduced into a biological system (e.g., a virus, prokaryotic or eukaryotic cell, zygote, embryo, plant, or animal, e.g., non-human animal). A prokaryotic cell may be a bacterial cell. A eukaryotic cell may be, e.g., a fungal (e.g., yeast), invertebrate (e.g., insect, worm), plant, vertebrate (e.g., mammalian, avian) cell. A mammalian cell may be, e.g., a mouse, rat, non-human primate, or human cell. A cell may be of any type, tissue layer, tissue, or organ of origin. In some embodiments a cell may be, e.g., an immune system cell such as a lymphocyte or macrophage, a fibroblast, a muscle cell, a fat cell, an epithelial cell, or an endothelial cell. A cell may be a member of a cell line, which may be an immortalized mammalian cell line capable of proliferating indefinitely in culture.

Applications of the methods described herein include, without limitation, in vivo CRISPR-based precision gene therapies for treating acquired or genetic diseases affecting a variety of cell types. In particular, the CRISPR duology and trilogy platforms described herein can be applied to cells, tissues, and organs, and also can be used for in vivo interrogation of endogenous genes using CRISPR activators and repressors, including CRISPR-mediated endogenous gene activation.

So that the compositions, methods, and systems provided herein may more readily be understood, certain terms are defined:

As used in this specification and the appended claims, the singular forms "a," "an," and "the" include plural references unless the context clearly dictates otherwise. Any reference to "or" herein is intended to encompass "and/or" unless otherwise stated.

The terms "comprising", "comprises" and "comprised of" as used herein are synonymous with "including", "includes" or "containing", "contains", and are inclusive or open-ended and do not exclude additional, non-recited members, elements, or method steps. The phraseology and terminology used herein is for the purpose of description and should not be regarded as limiting. The use of "including," "comprising," "having," "containing," "involving," and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

As used herein, the terms "synthetic" and "engineered" are used interchangeably and refer to the aspect of having been manipulated by the hand of man.

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or include non-naturally occurring nucleotides or nucleosides. Furthermore, the terms "nucleic acid," "DNA," "RNA," and/or similar terms include nucleic acid analogs, i.e., analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadeno sine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The terms "protein," "peptide," and "polypeptide" are used interchangeably herein and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. A protein may comprise different domains, for example, a nucleic acid binding domain and a nucleic acid cleavage domain. In some embodiments, a protein comprises a proteinaceous part, e.g., an amino acid sequence constituting a nucleic acid binding domain, and an organic compound, e.g., a compound that can act as a nucleic acid cleavage agent.

As used herein, "modifying" ("modify") one or more target nucleic acid sequences refers to changing all or a portion of a (one or more) target nucleic acid sequence and includes the cleavage, introduction (insertion), replacement, and/or deletion (removal) of all or a portion of a target nucleic acid sequence. All or a portion of a target nucleic acid sequence can be completely or partially modified using the methods provided herein. For example, modifying a target nucleic acid sequence includes replacing all or a portion of a target nucleic acid sequence with one or more nucleotides (e.g., an exogenous nucleic acid sequence) or removing or deleting all or a portion (e.g., one or more nucleotides) of a target nucleic acid sequence. Modifying the one or more target nucleic acid sequences also includes introducing or inserting one or more nucleotides (e.g., an exogenous sequence) into (within) one or more target nucleic acid sequences.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

EXAMPLE

This section describes design and characterization of a CRISPR/Cas9 system capable of performing simultaneous gene modification and repression. In particular, this section demonstrates as proof-of-principle use of a CRISPR/Cas9 tool for simultaneous gene modification and repression of endogenous expression of LigIV (DNA ligase IV non-homologous end joining DNA repair, also LIGIV). The protein encoded by LIGIV is a DNA ligase that joins single-strand breaks in a double-stranded polydeoxynucleotide in an ATP-dependent reaction. LigIV protein is considered to be essential for V(D)J recombination and DNA double-strand break (DSB) repair through nonhomologous end joining (NHEJ).

Materials and Methods

Vectors: pDRGFP (Addgene plasmid #26475) contains an enhanced green fluorescent protein (EGFP) gene, which was mutated through the inclusion of the 18-bp recognition sequence of the endonuclease I-SceI containing two stop codons, thereby disrupting expression of green fluorescent protein (GFP) (Pierce et al., 1999). Introduction of I-SceI into cells containing pDRGFP (or introduction of Cas9 and a gRNA targeting the I-SceI recognition sequence, as was performed in this study) results in a DSB at the site of mutation. Cells can then use a donor template also contained within pDRGFP to repair the DSB during HDR, thereby restoring the EGFP gene. The resulting GFP$^+$ cells can be quantified by flow cytometry, which acts as a reporter for HDR and successful gene editing.

Vector pX330-U6-Chimeric_BB-CBh-hSpCas9 (pX330) (Addgene plasmid #42230) was modified to include a gRNA targeting the mutated EGFP gene in pDRGFP. After a gRNA of interest is inserted into pX330, its expression is driven by a human U6 promoter (hU6).

As illustrated in FIG. 1, the gRNA for vector pJZC74 (Addgene plasmid #62342) included a 3' RNA hairpin sequence for com, which is connected to the gRNA by a short, 2-bp linker. Although pJZC74 was designed for use with dCas9 as a single master controller of transcriptional regulation (Zalatan et al., 2014), this study achieved repression using Cas9 in complex with 14-nt gRNAs. pJZC74 does not contain ideal restriction enzyme sites immediately flanking its gRNA which, if present, would allow a desired gRNA to be easily inserted. For its use in this study, pJZC74 was modified to include a customizable gRNA insert site, which was then utilized to insert a variety of gRNAs targeting LIGIV. hCas9 (Addgene plasmid #41815) was used in this study to supplement the Cas9 expressed by pX330.

Modification of pX330: As illustrated in FIG. 2, the gRNA inserted into pX330 was designed to induce a DSB in the mutated EGFP gene in pDRGFP. In the event of HDR, cells repaired the DSB using pDRGFP's donor template, resulting in green fluorescence. The 20-nt gRNA was designed with appropriate overhangs for insertion into pX330. An extra guanine nucleotide was included at the 5' end to promote optimal expression by the hU6 promoter in pX330 (Graham & Root, 2015).

Top and bottom single-stranded oligonucleotides (oligos) for the gRNA to be inserted into pX330 were ordered from Integrated DNA Technologies and received as dried down DNA. Each oligo was centrifuged upon receipt at 12000 g for 60 seconds to concentrate the dried DNA in the bottom of the tube. The oligos were individually reconstituted to a concentration of 100 μM using nuclease-free water. To anneal and kinase the top and bottom oligos, a 20 μL reaction was setup on ice in a PCR tube, including 2 μL of the top oligo (100 μM), 2 μL of the bottom oligo (100 μM), 2 μL of T4 DNA Ligase Buffer, 1 μL of T4 PNK, and 13 μL of nuclease-free water. After all components were added, the tube was tapped gently to mix and incubated in a thermocycler at 37° C. for 30 minutes, 95° C. for 5 minutes, then 25° C. for 2 minutes.

Figure 3A:
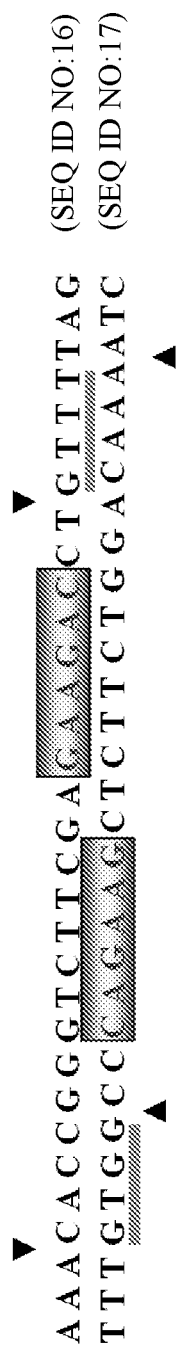
FIGS. 3A-3D illustrate insertion of gRNA targeting pDRGFP into pX330. (A) pX330 gRNA insert site before digestion. The pX330 gRNA insert site included BbsI recognition sites (gray shaded boxes). BbsI cut sites are indicated by arrows (▲▼). (B) pX330 following digestion. After digestion with BbsI (or one of its isoschizomers, such as BpiI), the gRNA insert site is removed leaving 4-bp overhangs (purple underline). (C) Annealed & kinased gRNA oligo targeting pDRGFP. The 20-bp gRNA (blue underline) was designed to include overhangs (red underline) complementary to the overhangs in the digested pX330 vector. The gRNA also included an extra guanine nucleotide (pink shaded box) to promote optimal expression by pX330's hU6 promoter (Graham & Root, 2015). (D) gRNA ligated into pX330. The gRNA was inserted into pX330 using Golden Gate Assembly.
Figure 3B:
Figure 3C:
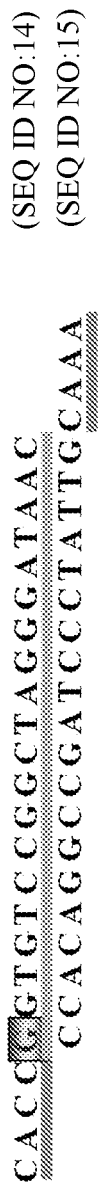
Figure 3D:
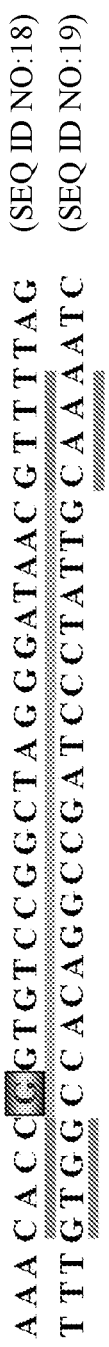

The gRNA for targeting the mutated EGFP gene in pDRGFP was ligated into pX330 using Golden Gate Assembly. The gRNA insert site in pX330 is flanked by two BbsI Type II restriction enzyme recognition sequences on opposing DNA strands (FIG. 3A). BpiI, an isoschizomer of BbsI, was used to digest pX330, leaving 4-bp overhangs at the gRNA insert site (FIG. 3B). The annealed and kinased gRNA oligo, designed to include overhangs complementary to the overhangs in the digested pX330, was then ligated into pX330 using Golden Gate Assembly, removing the BbsI recognition sequences (FIGS. 3C-3D).

To ligate the gRNA into pX330 using Golden Gate Assembly, the gRNA insert and vector were diluted to establish a 6:1 ratio of insert-to-vector. A 20 μL reaction was setup in a PCR tube on ice, including 1 μL of the diluted pX330 vector (100 ng), 1 μL of the diluted gRNA insert, 2 μL of T4 10× ligase buffer, 1 μL of T4 DNA ligase, 1.5 μL of the restriction enzyme BpiI, and 13.5 μL of nuclease-free water. After all components were added, the tube was tapped gently to mix and incubated in a thermocycler for 50 cycles of 37° C. for 10 minutes followed by 16° C. for 5 minutes. After these 50 cycles were complete, the temperature was raised to 50° C. for 5 minutes, then 80° C. for 5 minutes.

Before experimental use, the modified pX330 vector was transformed, inoculated, and the resulting DNA was extracted and purified by Miniprep, then digested and analyzed by gel electrophoresis to confirm appropriate band sizes were present. The vector was also sequenced to confirm the gRNA was successfully ligated into pX330.

Figure 4:
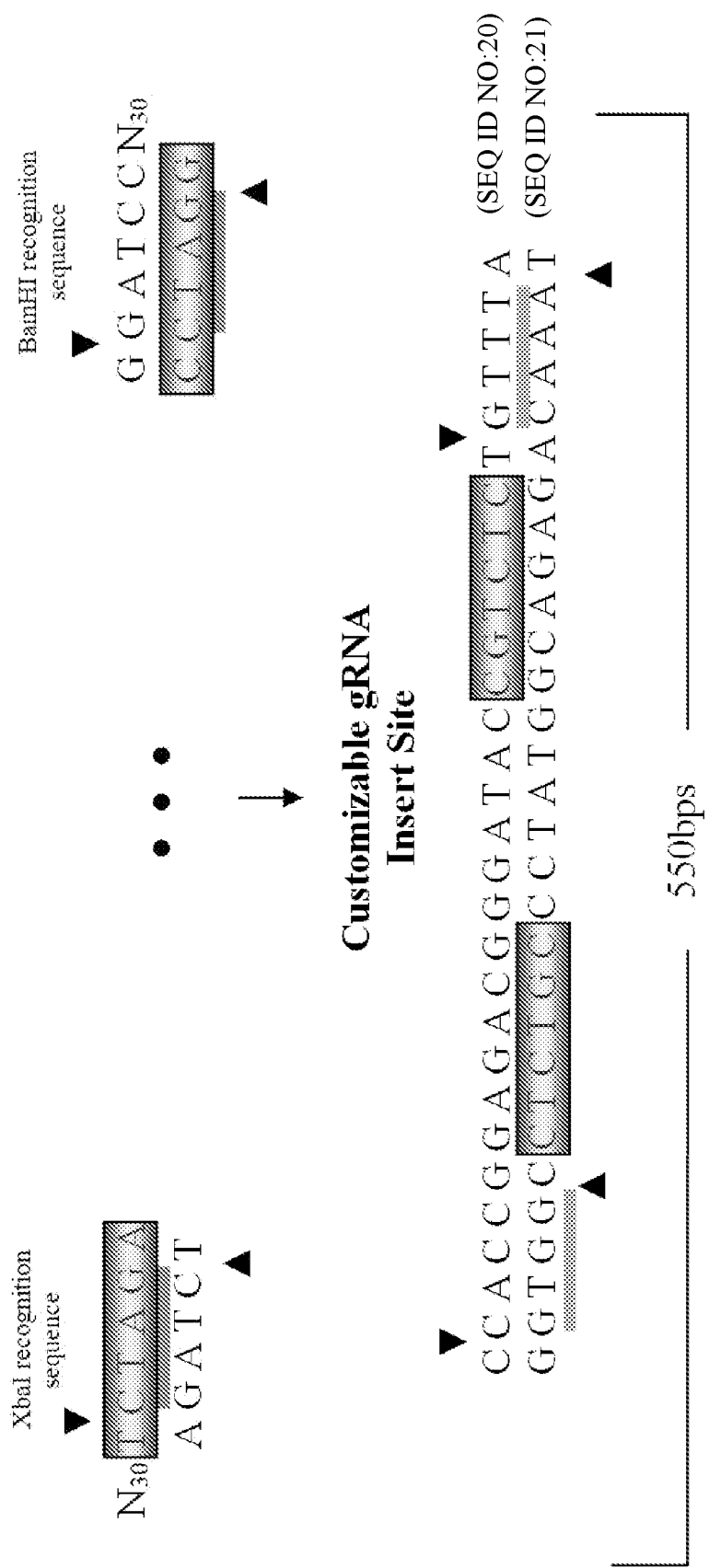
FIG. 4 illustrates a gBlock having a customizable gRNA insert site. The entire gBlock is 550 bps. Restriction enzyme cut sites are indicated by arrows (▲▼). Top: A small excess of base pairs flank both ends of the gBlock ($N_{30}$) to allow proper binding of XbaI and BamHI on their recognition sequences (gray shaded boxes) (Green & Sambrook, 2012). Overhangs remaining after digestion with XbaI and BamHI-HF are underlined in pink. Bottom: Customizable gRNA insert site includes BsmBI recognition sequences (gray shaded boxes). When digested with BsmBI, 4-bp overhangs (blue underline) remain for insertion of a gRNA of interest.

Modification of pJZC74: To enhance the modularity of pJZC74, a customizable gRNA insert site was designed and inserted into the vector. This gRNA insert site was then utilized to insert a variety of gRNAs targeting LIGIV. To facilitate insertion of the customizable gRNA insert site, a 550-bp gBlock was designed to be identical to a 550-bp section of pJZC74, with the exception of the customizable gRNA insert site that would replace pJZC74's original gRNA sequence. The gBlock was flanked on its ends by recognition sequences for the restriction enzymes XbaI and BamHI, which were used to create proper overhangs for insertion of the gBlock into pJZC74. As illustrated in FIG. 4, a customizable gRNA insert site was designed to include BsmBI recognition sequences, such that when the vector was digested with BsmBI, the customizable gRNA insert site was cut away, leaving overhangs complementary to the overhangs in any custom-designed gRNA to be inserted into pJZC74.

Figure 5A:
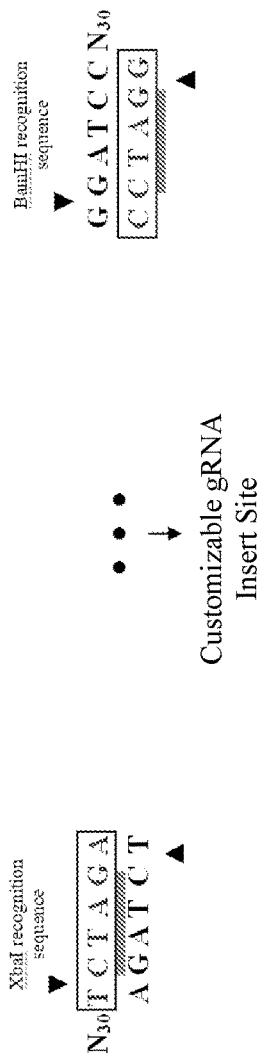
FIGS. 5A-5D illustrate insertion of gBlock containing customizable gRNA insert site into pJZC74.

Upon receipt, the gBlock was spun down and reconstituted in 10 μL of nuclease-free water, then briefly vortexed and spun down again. Prior to insertion of the gBlock into pJZC74, a small excess of nucleotides were digested off both outer ends of the gBlock using XbaI and BamHI-HF. This created overhangs in the gBlock that were complementary to the overhangs in linearized pJZC74. The gBlock was digested using a 50 μL reaction, including 10 μL of diluted gBlock, 2 μL of XbaI, 2 μL of BamHI-HF, 5 μL of CutSmart® Buffer, and 31 μL of nuclease-free water. This reaction was incubated for 2 hours at 37° C.

pJZC74 was linearized using restriction enzymes XbaI and BamHI-HF, whose recognition sequences flank the region of pJZC74 where the gBlock containing the customizable gRNA insert site was to be placed. See FIG. 5A. A 40 μL reaction was setup on ice using 10 μL of pJZC74, 2 μL of XbaI, 2 μL of BamHI-HF, 4 μL of CutSmart® Buffer, and 22 μL of nuclease-free water. Digestion was performed at 37° C. for 3 hours. When 30 minutes was remaining in the incubation period, calf-intestinal alkaline phosphatase was added. The digested vector was then gel purified, along with the digested gBlock.

Gel purification of linearized pJZC74 and the gBlock containing the customizable gRNA insert was performed using the QIAQuick Gel Extraction Kit, according to the kit instructions, with a 1% agarose gel prepared using UltraPure™ Low Melting Point Agarose. The gel was cast and a wide-toothed comb was placed to allow for adequate separation of samples.

After ~1 hour, 8 μL of 6× purple loading dye was added to linearized pJZC74 and the digested gBlock, which were then loaded into alternate wells in the gel. The gel electrophoresis apparatus was run at 150V. After an hour and a half, the samples were visualized using an Invitrogen Safe Imager™ 2.0, a blue light transilluminator. Based on the band sizes visualized, the desired DNA fragments were identified and extracted using a clean spatula. The gel fragments were transferred to individual, sterile microcentrifuge tubes and weighed. Buffer QG was added to the gels in an amount equal to 3× the weight of the gel. The tubes were then incubated in a 58° C. heat block for approximately 10 minutes to allow the gel to completely dissolve.

After briefly vortexing the samples, 100% isopropyl alcohol was added to each tube in a volume equal to 1× the weight of the gel in grams and mixed gently by pipette. 750 μL of this gel-solution was transferred to a spin column and centrifuged. (All centrifugation steps were performed at 12000 g for 1 minute.) The flow-through was discarded and the remaining gel-solution was added to the spin column and centrifuged. After again discarding the flow-through, 500 μL of Buffer PE was added to the spin column, the columns were centrifuged, and the flow-through was discarded. This was repeated two additional times, then a final dry spin centrifugation cycle was performed. The spin column was placed into a sterile microcentrifuge tube and 30 μL of nuclease-free water was added directly to the membrane. After 3-5 minutes, the tubes were centrifuged a final time to elute the DNA.

Figure 5B:
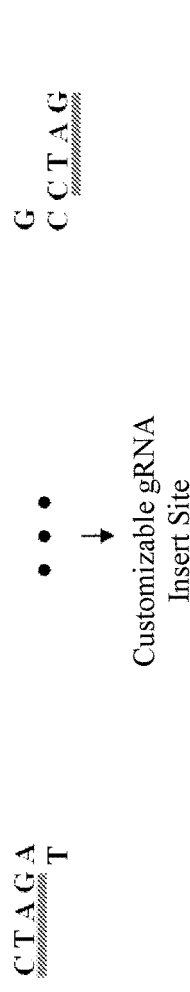
Figure 5C:
Figure 5D:
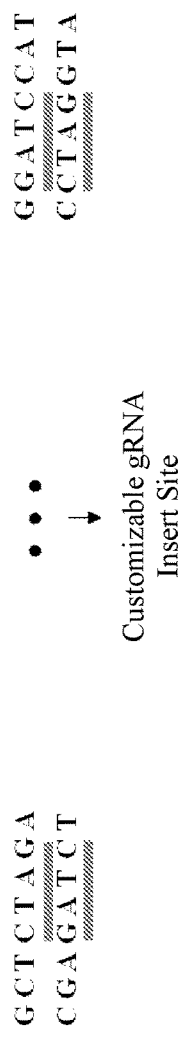

Following gel purification, the gBlock containing the customizable gRNA was ligated into pJZC74. See FIGS. 5B-5D. Ligation was performed using the New England Biolabs (NEB) Quick Ligation™ Kit. A 3-fold molar excess of the gBlock was combined with 50 ng of pJZC74. A 20 μL reaction was setup on ice with 1.2 μL of linearized pJZC74 (50 ng), 3 μL of the gBlock, 10 μL of 2× Quick Ligation Buffer, 1 μL of Quick T4 DNA Ligase, and 4.8 μL of nuclease-free water. Tubes were spun down and incubated at 25° C. for 10 minutes. The ligation reaction was held at −20° C. until ready for transformation, inoculation, and DNA purification. Successful ligation was confirmed by diagnostic digestion and sequencing. Following ligation, any gRNA targeting a gene of interest could be ligated into pJZC74 using the customizable gRNA insert site.

Figure 6:
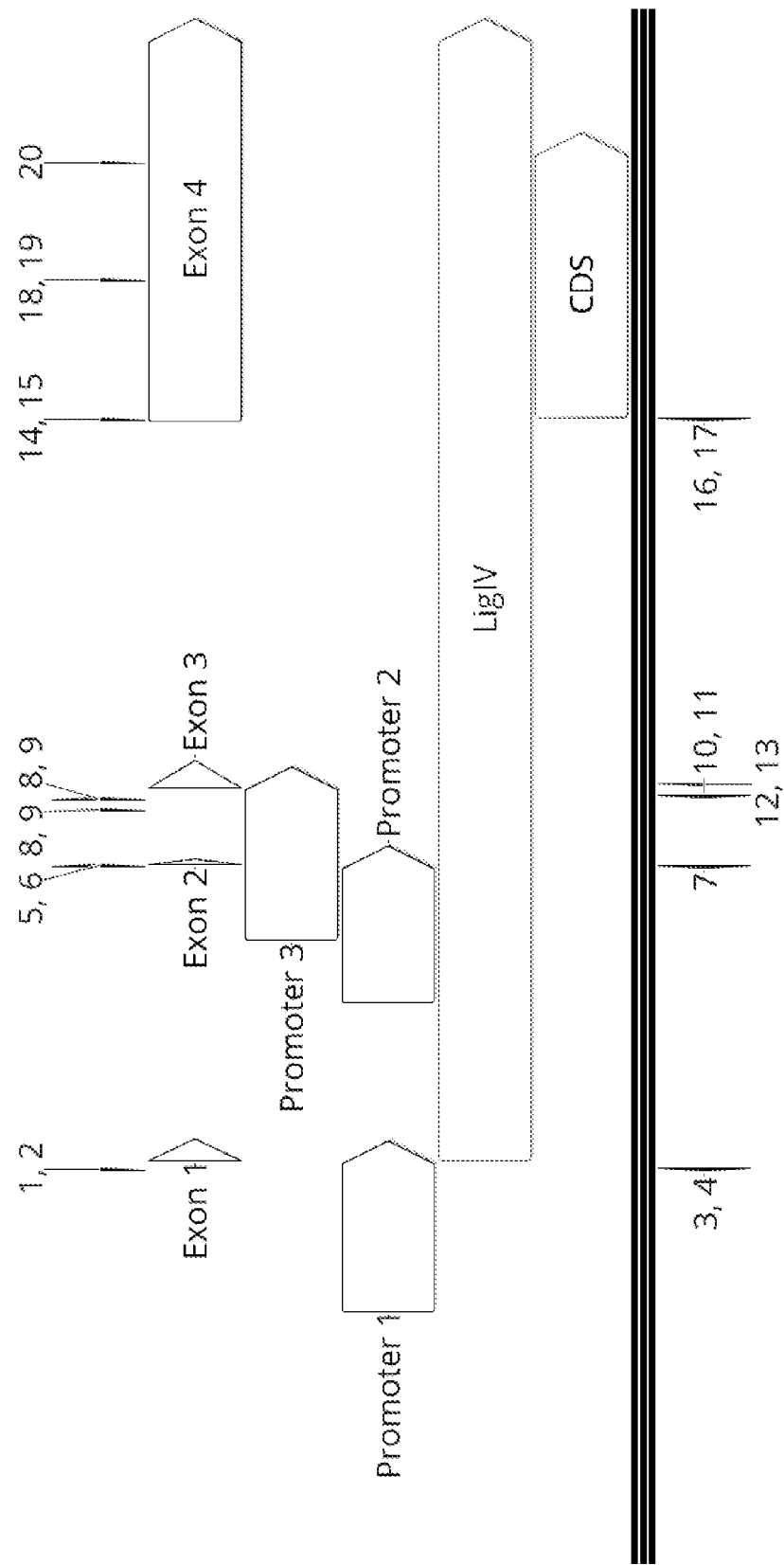
FIG. 6 illustrates key regions of LIGIV targeted by gRNAs. gRNAs target an array of regions within LIGIV, including its promoters, exons and the CDS of exon 4 (Zerbino et al., 2018). Complementary sequences for gRNAs 8 and 9 are each present twice in LIGIV.

Design of gRNAs Targeting LIGIV: Various gRNAs were inserted into pJZC74 for repression of LIGIV. The gRNAs were designed for robust testing of key regions of the LIGIV gene (Table 1 and FIG. 6). This includes targeting LIGIV's promoters and exons, as well as regions nearby and within the coding domain sequence (CDS) of exon 4 (Zerbino et al., 2018). Several gRNAs were tested on both DNA strands to assess whether there was any impact on repression efficiency. Sequences of gRNAs are presented in Table 7. Of these, gRNAs 1, 3, 5, 8, 12, 14, 16, 18, and 20 were placed into a pJZC74 vector that contained an extra TTGTT sequence, which preceded the gRNA in the backbone. The purpose of this short sequence was unclear from a review of relevant literature. Therefore, certain gRNAs were tested with and without this sequence.

TABLE 1

Description of Regions of LIGIV Targeted by gRNAs

| gRNA(s) | Region of LIGIV targeted |
|---|---|
| 1, 2 | Within promoter 1 |
|  | Within 100 bps of start of exon 1 |
| 3, 4 | Opposite strand of gRNA-1 & gRNA-2 |
| 5, 6 | Within promoter 2 & promoter 3 |
|  | Within 25 bps of start of exon 2 |
| 7 | Opposite strand of gRNA-5 & gRNA-6 |
| 8, 9* | Within promoter 3 |
|  | Within 250 bps of start of exon 3 |
| 10, 11 | Opposite strand of gRNA-8 & gRNA-9 (first set) |
| 12, 13 | Opposite strand of gRNA-8 & gRNA-9 (second set) |
| 14, 15 | Within first 50 bps of exon 4 |
|  | At start of CDS of exon 4 |
| 16, 17 | Opposite strand of gRNA-14 & gRNA-15 |
| 18, 19 | Within CDS of exon 4 |
| 20 | Near end of CDS of exon 4 |
|  | Region previously targeted for knockout of LIGIV (Shalem et al., 2014) |

*Complementary sequences for gRNA-8 and gRNA-9 are present twice in LIGIV.

Golden Gate Assembly of gRNAs Targeting LIGIV Into pJZC74: Top and bottom gRNA oligos designed to target LIGIV were previously annealed and kinased. To ligate each gRNA insert into pJZC74 using Golden Gate Assembly, individual 20 μL reactions were setup in PCR tubes on ice, including 6.5 μL of pJZC74 (100 ng), 6 μL of the gRNA insert, 3 μL of nuclease-free water, 2 μL of T4 10× ligase buffer, 1 μL of T4 DNA ligase, and 1.5 μL of the restriction enzyme BsmBI. BsmBI was used to digest the customizable gRNA insert site in pJZC74, creating overhangs for insertion of the gRNA. After the reactions were setup, PCR tubes were added to a thermocycler and run for 50 cycles of 37° C. for 10 minutes followed by 16° C. for 5 minutes. Following completion of these 50 cycles, the temperature was raised to 50° C. for 5 minutes, then 80° C. for 5 minutes.

Figure 7A:
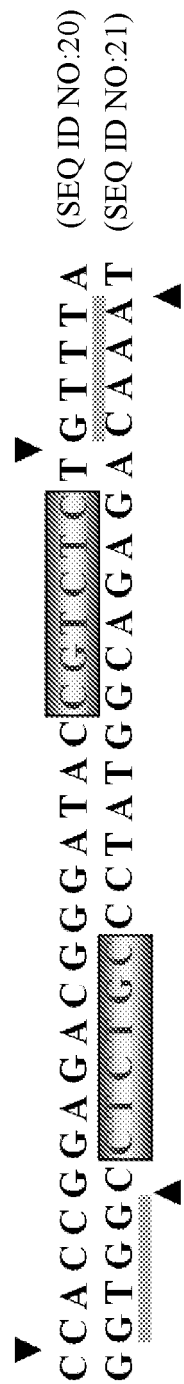
FIGS. 7A-7C illustrates insertion of gRNA of interest into pJZC74. (A) Customizable gRNA insert site before digestion. BsmBI recognition sequences (gray shaded boxes) were used to digest pJZC74. BsmBI cut sites are indicated by arrows (▲▼). (B) Customizable gRNA insert site after digestion. Following digestion with BsmBI, the customizable gRNA insertion site was cut away and overhangs remained (blue underline). (C) gRNA targeting LIGIV ligated into pJZC74. A 14-bp gRNA ($N_{14}$) targeting LIGIV was then ligated into pJZC74 using Golden Gate Assembly.
Figure 7B:
Figure 7C:
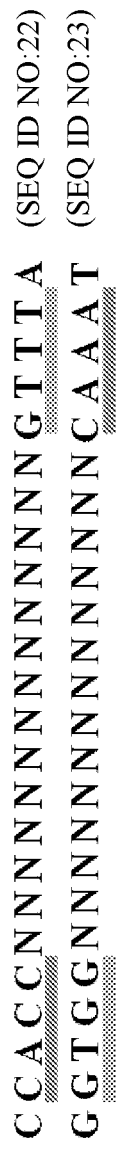

Before experimental use, the modified vectors were transformed using high-fidelity 5-alpha *E. coli* cells, inoculated, and the resulting DNA was extracted and purified by Miniprep, then digested and analyzed by gel electrophoresis to confirm appropriate band sizes were present. After a gRNA of interest was inserted, the BsmBI sites were no longer present (FIGS. 7A-7C).

Extracted DNA was transfected into human embryonic kidney (HEK) cells. Transfections were generally performed when HEK cells were 60-90% confluent, as confirmed by microscope analysis. DNA samples were prepared in duplicate for fluorescence-activated cell sorting (FACS) analysis and in quadruplicate if quantitative polymerase chain reaction (qPCR) analysis was also to be performed. All transfections were performed using sterile technique within a biosafety cabinet.

DNA samples were diluted to the desired concentrations by mixing DNA with an appropriate volume of nuclease-free water in sterile 1.5 μL microcentrifuge tubes. A DNA mix was then prepared by adding an appropriate volume of the desired DNA components to sterile 1.5 μL microcentrifuge tubes. The total DNA concentration per well was normalized across all tubes by adding non-coding DNA, as appropriate.

To prepare for transfection, polyethylenimine (PEI) was removed from the −80° C. freezer and allowed to thaw. The thawed PEI was vortexed and an appropriate amount was aliquoted to a sterile 1.5 μL microcentrifuge tube in a volume necessary to achieve a 2:1 ratio of PEI-to-DNA per well. An appropriate volume of serum-free DMEM was added to the PEI, such that a total volume of 25 μL of the DMEM-PEI solution would be available for each well.

An appropriate volume of serum-free DMEM was added to each DNA mix sufficient to bring the total volume of the DMEM-DNA solution to 25 μL for each well designated to receive the DNA components. The aliquoted DMEM-PEI solution was vigorously vortexed, and the appropriate volume was added to each DMEM-DNA mix. Each reaction was vortexed twice for two seconds immediately after adding the DMEM-PEI solution. All reactions were allowed to sit for 30 minutes within the biosafety cabinet. During this time, the DMEM was changed on the previously-seeded 24-well plates. After 30 minutes, each reaction was individually pipetted once to mix, and 50 μL of each reaction was added to each designated well in drops. At appropriate intervals, the transfection plate was tilted and swirled gently to distribute.

After all transfection components were added to the 24-well plate, the plate was returned to the 37° C./5% $CO_2$ incubator. DMEM was changed every 24 hours. FACS analysis was generally performed after 72 hours. qPCR analysis was also performed after 72 hours or RNA was extracted and stored at −80° C. until ready for use.

Results

Figure 8:
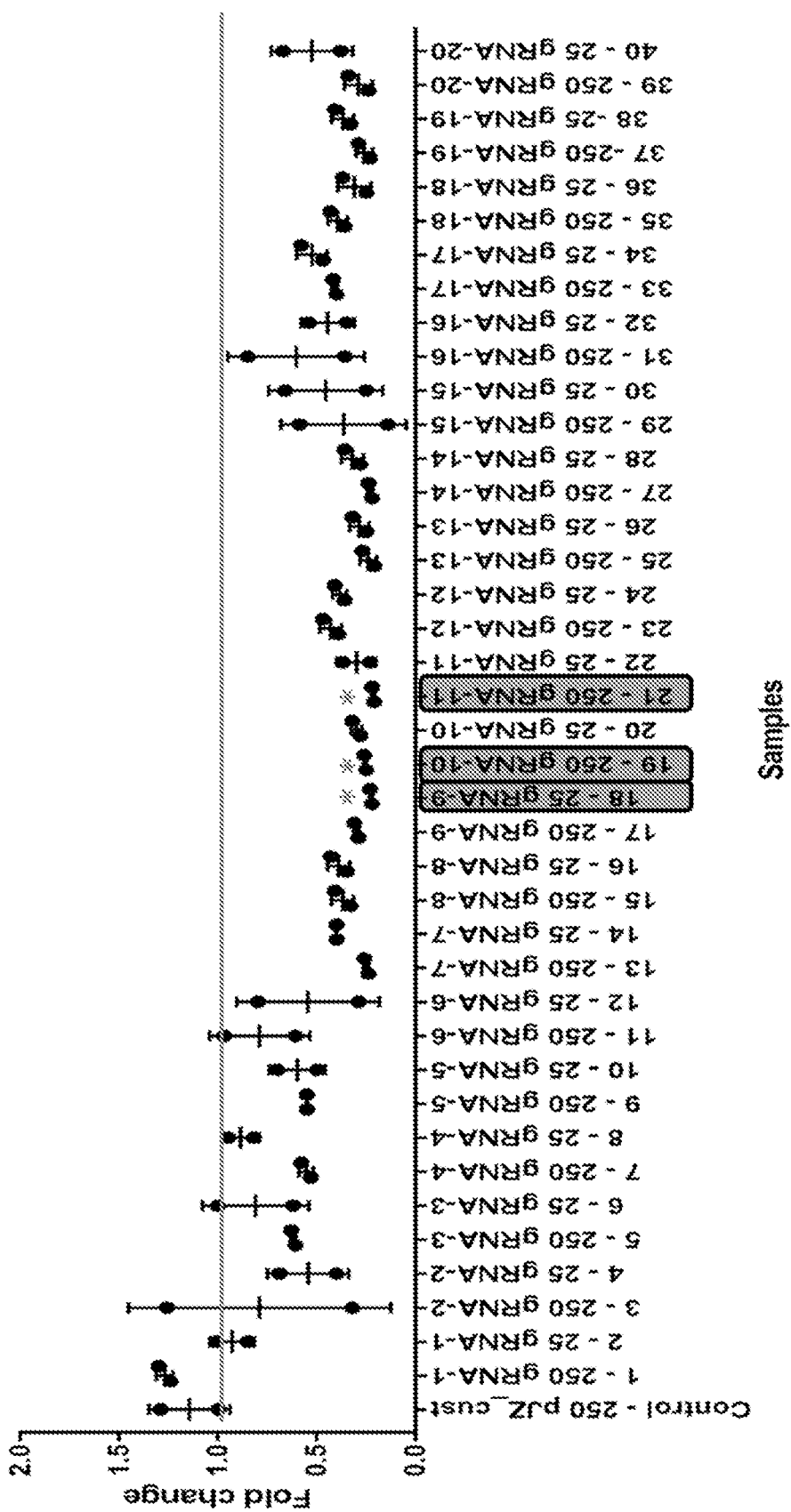
FIG. 8 demonstrates repression of LIGIV by gRNAs. The control qPCR sample contained pJZC74 with the customizable gRNA insert site, but no gRNA. Anything below the control (1.0) indicates LIGIV repression. qPCR samples 18, 19 and 21, containing gRNA-9, gRNA-10 and gRNA-11 respectively, showed significant repression of LIGIV and were selected for further analysis.

An initial transfection in HEK cells was performed, with samples receiving the components listed in Table 2. Twenty gRNAs, each in its own pJZC74 vector, were initially tested at both 250 ng and 25 ng with a corresponding amount of hCas9. Each sample received 20 ng of EBFP as a transfection control. Following transfection, RNA extraction and cDNA synthesis, qPCR was performed to measure the expression of LIGIV. As shown in FIG. 8, several gRNAs achieved robust repression of LIGIV.

TABLE 2

Components of Transfection for Initial Screening of LIGIV gRNAs

| Sample | Components |
|---|---|
| Control | 20 ng EBFP + 250 ng pJZC74 with customizable gRNA insert site |
| 1 | 20 ng EBFP + 250 ng gRNA-1 + 250 ng hCas9 |
| 2 | 20 ng EBFP + 25 ng gRNA-1 + 25 ng hCas9 |

TABLE 2-continued

Components of Transfection for Initial Screening of LIGIV gRNAs

| Sample | Components |
|---|---|
| 3 | 20 ng EBFP + 250 ng gRNA-2 + 250 ng hCas9 |
| 4 | 20 ng EBFP + 25 ng gRNA-2 + 25 ng hCas9 |
| 5 | 20 ng EBFP + 250 ng gRNA-3 + 250 ng hCas9 |
| 6 | 20 ng EBFP + 25 ng gRNA-3 + 25 ng hCas9 |
| 7 | 20 ng EBFP + 250 ng gRNA-4 + 250 ng hCas9 |
| 8 | 20 ng EBFP + 25 ng gRNA-4 + 25 ng hCas9 |
| 9 | 20 ng EBFP + 250 ng gRNA-5 + 250 ng hCas9 |
| 10 | 20 ng EBFP + 25 ng gRNA-5 + 25 ng hCas9 |
| 11 | 20 ng EBFP + 250 ng gRNA-6 + 250 ng hCas9 |
| 12 | 20 ng EBFP + 25 ng gRNA-6 + 25 ng hCas9 |
| 13 | 20 ng EBFP + 250 ng gRNA-7 + 250 ng hCas9 |
| 14 | 20 ng EBFP + 25 ng gRNA-7 + 25 ng hCas9 |
| 15 | 20 ng EBFP + 250 ng gRNA-8 + 250 ng hCas9 |
| 16 | 20 ng EBFP + 25 ng gRNA-8 + 25 ng hCas9 |
| 17 | 20 ng EBFP + 250 ng gRNA-9 + 250 ng hCas9 |
| 18 | 20 ng EBFP + 25 ng gRNA-9 + 25 ng hCas9 |
| 19 | 20 ng EBFP + 250 ng gRNA-10 + 250 ng hCas9 |
| 20 | 20 ng EBFP + 25 ng gRNA-10 + 25 ng hCas9 |
| 21 | 20 ng EBFP + 250 ng gRNA-11 + 250 ng hCas9 |
| 22 | 20 ng EBFP + 25 ng gRNA-11 + 25 ng hCas9 |
| 23 | 20 ng EBFP + 250 ng gRNA-12 + 250 ng hCas9 |
| 24 | 20 ng EBFP + 25 ng gRNA-12 + 25 ng hCas9 |
| 25 | 20 ng EBFP + 250 ng gRNA-13 + 250 ng hCas9 |
| 26 | 20 ng EBFP + 25 ng gRNA-13 + 25 ng hCas9 |
| 27 | 20 ng EBFP + 250 ng gRNA-14 + 250 ng hCas9 |
| 28 | 20 ng EBFP + 25 ng gRNA-14 + 25 ng hCas9 |
| 29 | 20 ng EBFP + 250 ng gRNA-15 + 250 ng hCas9 |
| 30 | 20 ng EBFP + 25 ng gRNA-15 + 25 ng hCas9 |
| 31 | 20 ng EBFP + 250 ng gRNA-16 + 250 ng hCas9 |
| 32 | 20 ng EBFP + 25 ng gRNA-16 + 25 ng hCas9 |
| 33 | 20 ng EBFP + 250 ng gRNA-17 + 250 ng hCas9 |
| 34 | 20 ng EBFP + 25 ng gRNA-17 + 25 ng hCas9 |
| 35 | 20 ng EBFP + 250 ng gRNA-18 + 250 ng hCas9 |
| 36 | 20 ng EBFP + 25 ng gRNA-18 + 25 ng hCas9 |
| 37 | 20 ng EBFP + 250 ng gRNA-19 + 250 ng hCas9 |
| 38 | 20 ng EBFP + 25 ng gRNA-19 + 25 ng hCas9 |
| 39 | 20 ng EBFP + 250 ng gRNA-20 + 250 ng hCas9 |
| 40 | 20 ng EBFP + 25 ng gRNA-20 + 25 ng hCas9 | gRNAs 9, 10 and 11 all achieved robust repression of LIGIV following initial qPCR analysis and were selected for further testing. These gRNAs all fall within promoter 3 and within ~250 bps of the start of exon 3. Successful ligation of these select gRNAs into pJZC74 was confirmed by diagnostic digestion and sequencing.

Figure 9A:
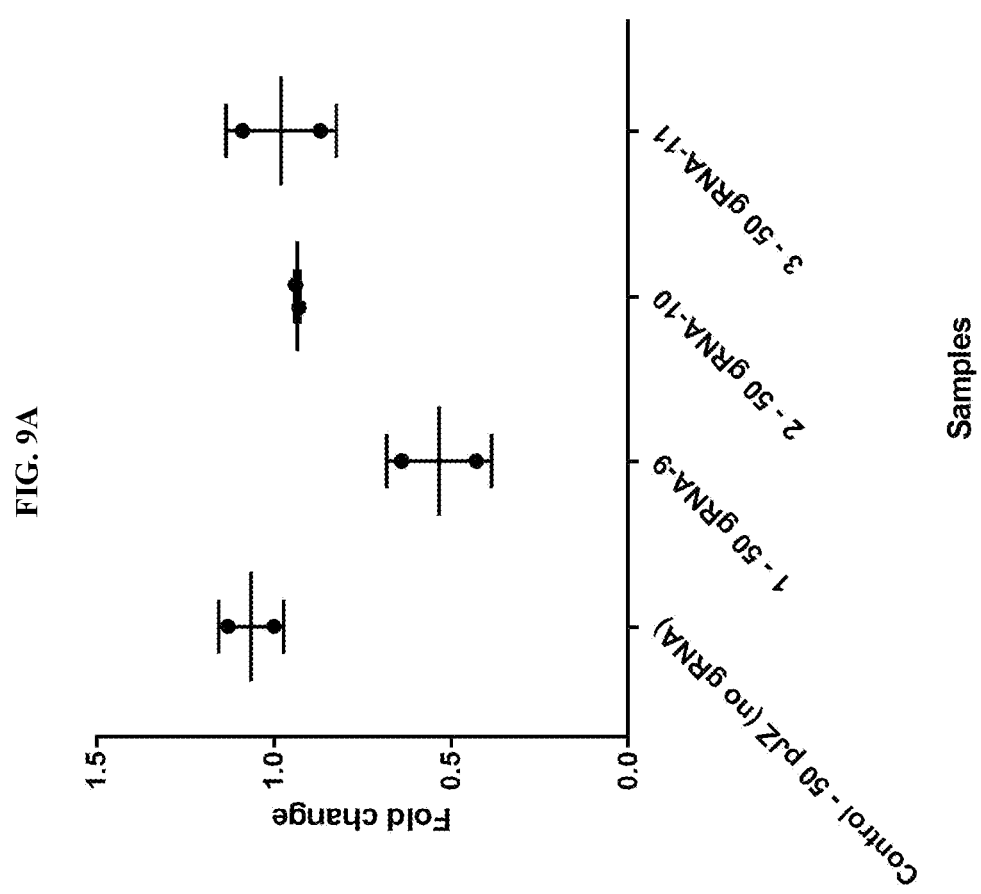
FIGS. 9A-9B demonstrate repression of LIGIV using select gRNAs. Control samples at 50 ng and 100 ng received the same components as the other samples, except pJZC74 only contained the customizable gRNA insert site. An appropriate amount of non-coding DNA was added, as needed, to normalize the total amount of DNA per well to ~570 ng. At 50 ng of pJZC74 (top), gRNA-9 achieved the most repression of LIGIV. At 100 ng of pJZC74 (bottom), gRNA-11 was the best-performing gRNA.
Figure 9B:
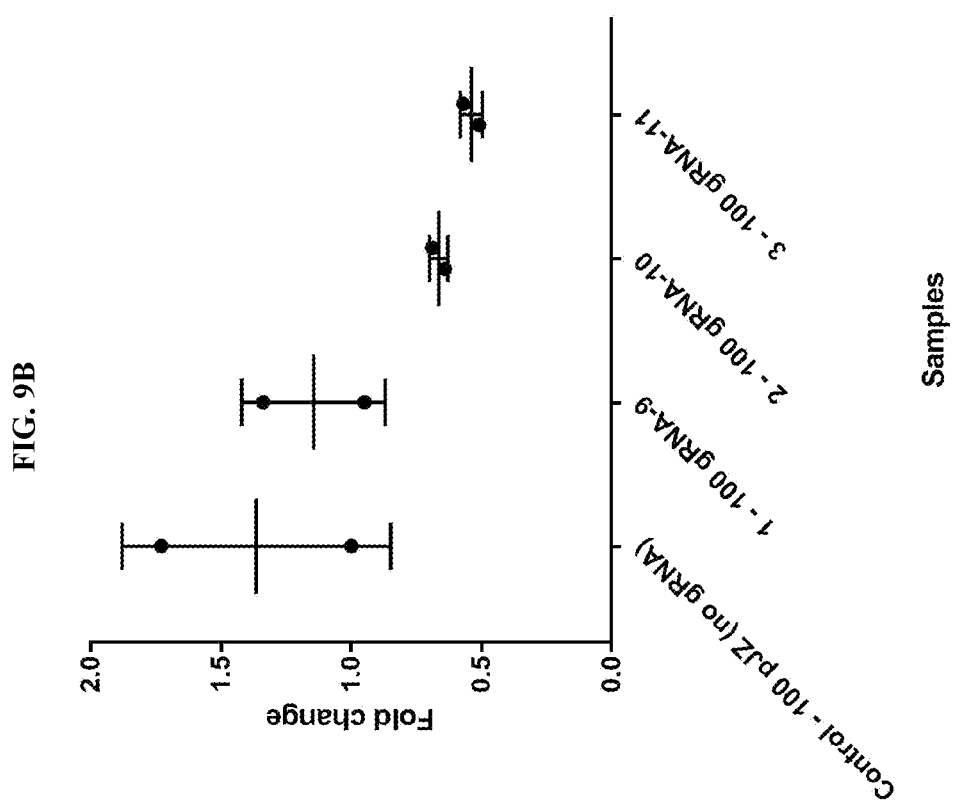

An additional transfection in HEK cells was performed, with each sample receiving the components listed in Table 3 and Table 4. Each gRNA was tested at 50 ng and 100 ng of pJZC74 (containing the indicated gRNA) with a corresponding amount of pX330 (containing the gRNA targeting pDRGFP) and hCas9 (50 ng or 100 ng) and 250 ng of pDRGFP. All samples received 20 ng of EBFP as a transfection control. Following transfection, RNA extraction and cDNA synthesis, qPCR was performed to assess the resulting repression of endogenous LIGIV gene expression (FIGS. 9A and 9B).

Figure 10A:
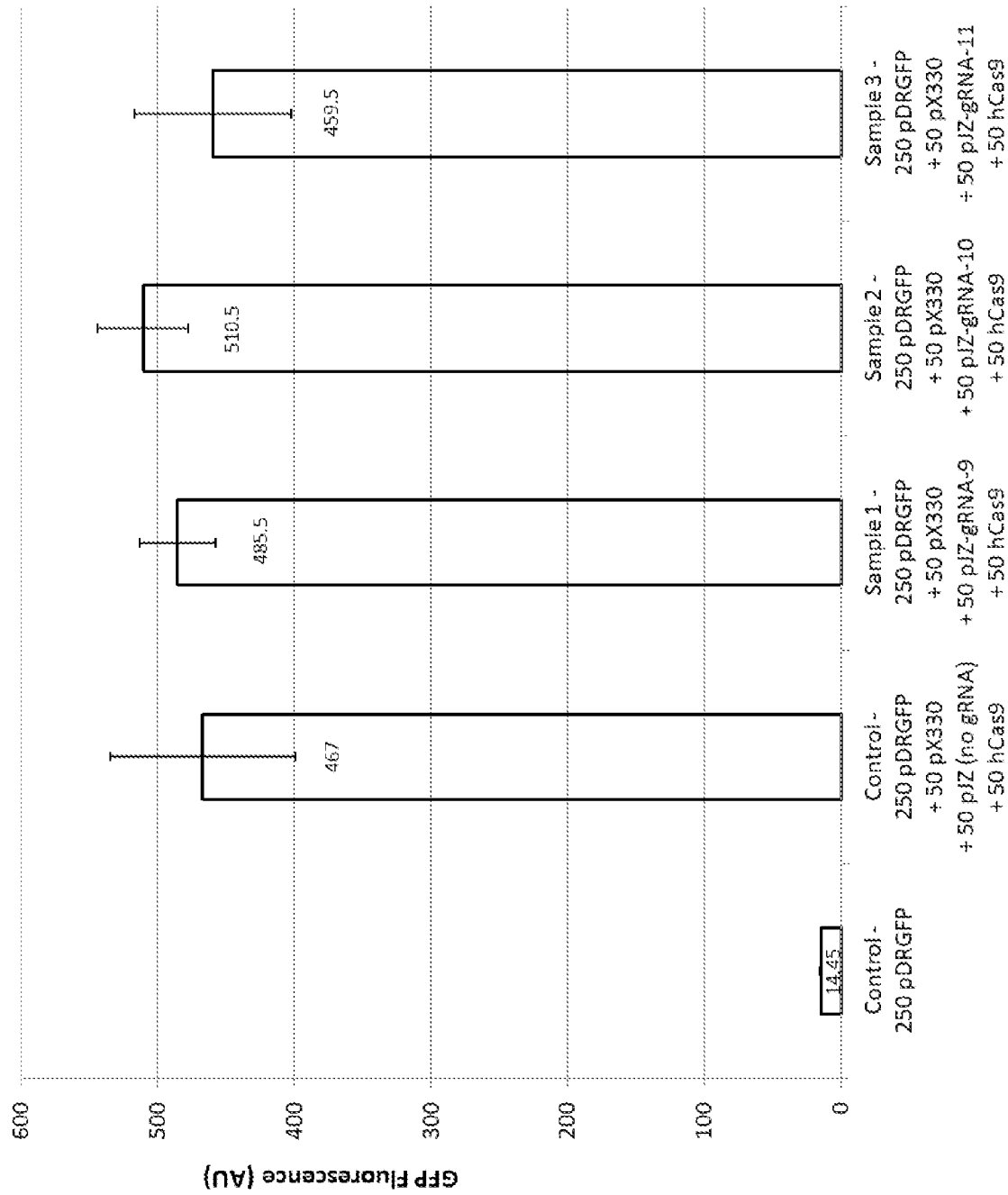
FIGS. 10A-10B show FACS results showing geometric mean of GFP+ cells. Non-coding DNA was added to normalize the total amount of DNA per well to ~570 ng.
Figure 10B:
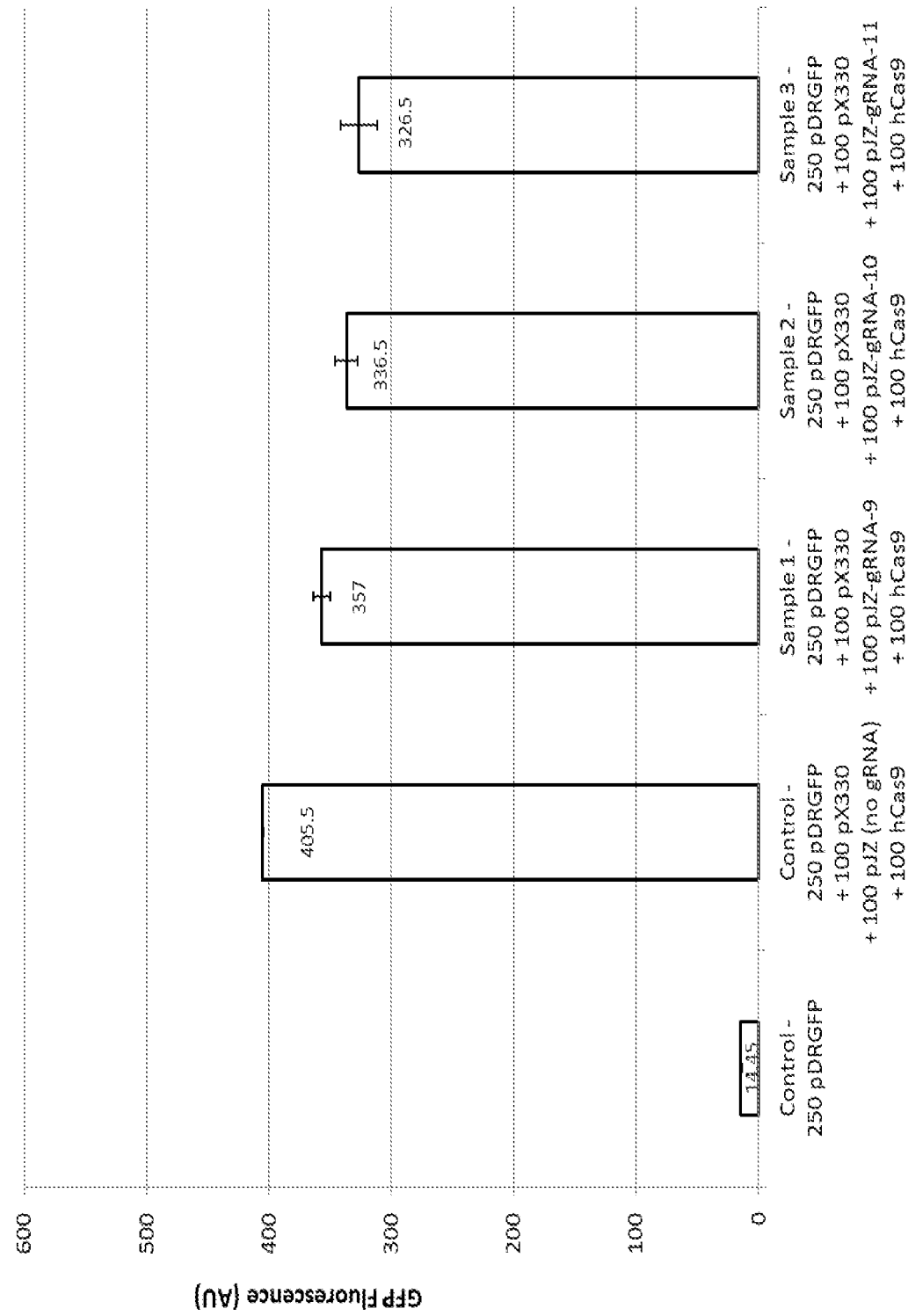

The same components transfected into HEK293FT cells to test for repression of endogenous LIGIV gene expression using qPCR analysis were also transfected to test for gene editing using FACS analysis. Each sample received the components listed in Table 5 and Table 6. Each gRNA was tested at 50 ng and 100 ng of pJZC74 (containing the indicated gRNA) with a corresponding amount of pX330 targeting pDRGFP and hCas9 (50 ng or 100 ng), as well as 250 ng of pDRGFP. As shown in FIGS. 10A-10B, FACS analysis revealed high levels of GFP compared to a control containing only pDRGFP, indicating that HDR repair and, therefore, gene editing occurred.

TABLE 3

Components of Transfection with 50 ng of pJZC74 for qPCR Analysis.

| Sample | Components |
|---|---|
| Control | 20 ng EBFP + 250 ng pDRGFP + 50 ng pX330 + 50 ng pJZC74 (no gRNA) + 50 ng hCas9 |
| 1 | 20 ng EBFP + 250 ng pDRGFP + 50 ng pX330 + 50 ng pJZC74-gRNA-9 + 50 ng hCas9 |
| 2 | 20 ng EBFP + 250 ng pDRGFP + 50 ng pX330 + 50 ng pJZC74-gRNA-10 + 50 ng hCas9 |
| 3 | 20 ng EBFP + 250 ng pDRGFP + 50 ng pX330 + 50 ng pJZC74-gRNA-11 + 50 ng hCas9 |

TABLE 4

Components of Transfection with 100 ng of pJZC74 for qPCR Analysis.

| Sample | Components |
|---|---|
| Control | 20 ng EBFP + 250 ng pDRGFP + 100 ng pX330 + 100 ng pJZC74 (no gRNA) + 100 ng hCas9 |
| 1 | 20 ng EBFP + 250 ng pDRGFP + 100 ng pX330 + 100 ng pJZC74-gRNA-9 + 100 ng hCas9 |
| 2 | 20 ng EBFP + 250 ng pDRGFP + 100 ng pX330 + 100 ng pJZC74-gRNA-10 + 100 ng hCas9 |
| 3 | 20 ng EBFP + 250 ng pDRGFP + 100 ng pX330 + 100 ng pJZC74-gRNA-11 + 100 ng hCas9 |

TABLE 5

Components of Transfection with 50 ng of pJZC74 for FACS Analysis.

| Sample | Components |
|---|---|
| Control | 20 ng EBFP + 250 ng pDRGFP |
| Control | 20 ng EBFP + 250 ng pDRGFP + 50 ng pX330 + 50 ng pJZC74 (no gRNA) + 50 ng hCas9 |
| 1 | 20 ng EBFP + 250 ng pDRGFP + 50 ng pX330 + 50 ng pJZC74-gRNA-9 + 50 ng hCas9 |
| 2 | 20 ng EBFP + 250 ng pDRGFP + 50 ng pX330 + 50 ng pJZC74-gRNA-10 + 50 ng hCas9 |
| 3 | 20 ng EBFP + 250 ng pDRGFP + 50 ng pX330 + 50 ng pJZC74-gRNA-11 + 50 ng hCas9 |

TABLE 6

Components of Transfection with 100 ng of pJZC74 for FACS Analysis.

| Sample | Components |
|---|---|
| Control | 20 ng EBFP + 250 ng pDRGFP |
| Control | 20 ng EBFP + 250 ng pDRGFP + 100 ng pX330 + 100 ng pJZC74 (no gRNA) + 100 ng hCas9 |
| 1 | 20 ng EBFP + 250 ng pDRGFP + 100 ng pX330 + 100 ng pJZC74-gRNA-9 + 100 ng hCas9 |
| 2 | 20 ng EBFP + 250 ng pDRGFP + 100 ng pX330 + 100 ng pJZC74-gRNA-10 + 100 ng hCas9 |
| 3 | 20 ng EBFP + 250 ng pDRGFP + 100 ng pX330 + 100 ng pJZC74-gRNA-11 + 100 ng hCas9 |

TABLE 7

Sequences of gRNAs Targeting LIGIV.

| | |
|---|---|
| 1 | GGCAAATGCCCCCGC (SEQ ID NO: 1) |
| 2 | GGCAAATGCCCCCGC (SEQ ID NO: 1) |
| 3 | GGCGGGGGCATTTGC (SEQ ID NO: 2) |
| 4 | GGCGGGGGCATTTGC (SEQ ID NO: 2) |

TABLE 7-continued

Sequences of gRNAs Targeting LIGIV.

| 5 | GCGGCGAGCAGCTGG (SEQ ID NO: 3) |
| 6 | GCGGCGAGCAGCTGG (SEQ ID NO: 3) |
| 7 | GGCTGCTCGCCGCGC (SEQ ID NO: 4) |
| 8* | GGTGTCTGGGACGTC (SEQ ID NO: 5) |
| 9* | GGTGTCTGGGACGTC (SEQ ID NO: 5) |
| 10 | GACCTGACGCCCCTC (SEQ ID NO: 6) |
| 11 | GACCTGACGCCCCTC (SEQ ID NO: 6) |
| 12 | GAGTCTACAGCGCTG (SEQ ID NO: 7) |
| 13 | GAGTCTACAGCGCTG (SEQ ID NO: 7) |
| 14 | GCATCACCGCTTTGA (SEQ ID NO: 8) |
| 15 | GCATCACCGCTTTGA (SEQ ID NO: 8) |
| 16 | GGGCAGCCATCAAAG (SEQ ID NO: 9) |
| 17 | GGGCAGCCATCAAAG (SEQ ID NO: 9) |
| 18 | GGACAAAAGAGGTGA (SEQ ID NO: 10) |
| 19 | GGACAAAAGAGGTGA (SEQ ID NO: 10) |
| 20 | GTCGACGCCACACCGTTTATT (SEQ ID NO: 11) |

*Complementary sequences for gRNAs 8 and 9 each appear twice in LIGIV.

TABLE 8

14-nt and 20-nt gRNA seqeunces Targeting LIGIV.

| 1/2 | GCAAATGCCCCGC (SEQ ID NO: 24) |
| 3/4 | GCGGGGGCATTTGC (SEQ ID NO: 25) |
| 5/6 | CGGCGAGCAGCTGG (SEQ ID NO: 26) |
| 7 | GCTGCTCGCCGCGC (SEQ ID NO: 27) |
| 8/9* | GTGTCTGGGACGTC (SEQ ID NO: 28) |
| 10/11 | ACCTGACGCCCCTC (SEQ ID NO: 29) |
| 12/13 | AGTCTACAGCGCTG (SEQ ID NO: 30) |
| 14/15 | CATCACCGCTTTGA (SEQ ID NO: 31) |
| 16/17 | GGCAGCCATCAAAG (SEQ ID NO: 32) |
| 18/19 | GACAAAAGAGGTGA (SEQ ID NO: 33) |
| 20 | TCGACGCCACACCGTTTATT (SEQ ID NO: 34) |

Discussion

An initial screen of gRNAs was performed to test which gRNAs were the most effective at repressing LIGIV. Twenty gRNAs were designed to target key regions of the LIGIV gene. These gRNAs were screened for repression of LIGIV, with cells receiving 20 ng of EBFP as a control for transfection, 250 ng or 25 ng of pJZC74 with a gRNA targeting LIGIV, and a corresponding amount (250 ng or 25 ng) of hCas9. If successful, each 14-nt gRNA targeting LIGIV with the Com-KRAB effector domain attached forms a ribonucleoprotein complex with hCas9. When the gRNA binds to its targeted region of the LIGIV gene, repression of LIGIV is achieved due to the chromatin-modifying effects of KRAB as described by Groner et al., 2010. Cas9 does not induce a DSB because the gRNAs are truncated at 14 nts. Several gRNAs showed significant repression of LIGIV. See FIG. 8.

An additional experiment was performed to corroborate the earlier findings of LIGIV repression and to further test whether simultaneous gene editing was occurring. Three high-performing gRNAs (9, 10 and 11) were selected for further study. The 20-nt gRNA in pX330 targeted the mutated EGFP in pDRGFP and the 14-nt gRNA in pJZC74 targeted LIGIV, each in complex with hCas9. Because pX330's gRNA was 20-nt, hCas9 induced a DSB in the EGFP gene, prompting cells to repair the cut site. If cells performed HDR using the donor template present in pDRGFP, GFP+ cells resulted. Alternatively, if cells performed NHEJ, indels likely occurred and the EGFP sequence remained disrupted. As with the initial screen, the 14-nt gRNAs in pJZC74 bind to LIGIV and Cas9 does not induce a DSB. This allows the KRAB effector domain to repress LIGIV without any genome modification.

HEK cells were transfected and analyzed contemporaneously by FACS and qPCR. For qPCR, cells received 250 ng of pDRGFP, 50 ng or 100 ng of pJZC74 (containing a gRNA targeting LIGIV), and a corresponding amount (50 ng or 100 ng) of both pX330 and hCas9. A control received the same components in the same concentrations as the remaining samples, except that pJZC74 only contained the customizable gRNA insert site (no gRNA targeting the human genome was present). As shown in FIGS. 9A-9B, qPCR analysis of gRNAs 9, 10 and 11 revealed that all three gRNAs repressed LIGIV.

For FACS, cells received the same components as were transfected for qPCR analysis. Two controls were included, one containing only 250 ng of pDRGFP and another with all the same components in the same concentrations as the remaining samples, except pJZC74 did not contain a gRNA. The results presented in FIGS. 10A-10B showed abundant GFP+ cells compared to the control without pX330, demonstrating that gene editing was occurring.

The overall results demonstrate successful simultaneous gene editing and transcriptional regulation using the CRISPR/Cas9 tool disclosed herein. Such a tool has important implications for the development of gene therapies, whereby the repression of key genes during genome editing may aid with the study and implementation of a host of disease treatments. Furthermore, repressing key genes involved with NHEJ during genomic editing may benefit the efficiency of HDR, thereby improving the efficiency with which desired genomic edits are performed.

The modified pJZC74 repression vector used for these studies was unique in that it was designed to recruit RNA-binding effector domains (e.g., KRAB-MecP2, MS2-KRAB-MecP2, and Com-KRAB) directly to the gRNA (via the com recruitment domain), rather than fusing the effector domain directly to dCas9 (Zalatan et al., 2014). This design enabled the use of catalytically-active Cas9 in some embodiments as the platform for transcriptional regulation, rather than dCas9, in conjunction with 14-nt gRNAs. In particular, this study expanded upon earlier findings by demonstrating repression using 14-nt gRNAs targeted to the genome, rather than a plasmid-based assay. Whereas gene repression through steric blocking alone using 14-nt gRNAs had been tested on gRNAs targeted in close proximity to an engineered TATA box (Kiani et al., 2014; Kiani et al., 2015), the approaches described herein overcome initial design constraints by effectuating gene silencing through long-range distribution of repressive chromatin modifiers along the target gene. Consequently, a broader selection of target sites is now available when designing repression experiments using CRISPR/Cas9.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the appended claims.

The invention claimed is:

1. A method for efficient Homology-Directed repair (HDR)-based gene editing, the method comprising introducing into an isolated recombinant host cell:

(a) at least one truncated guide RNA (gRNA) of 15 or less nucleotides (nt) in length complementary to at least a portion of a nucleotide sequence encoding a non-homologous end joining (NHEJ)-associated enzyme selected from the group consisting of DNA ligase IV (LigIV), XRCC4, XRCC5 (KU80), and XRCC6 (KU70);

(b) at least one gRNA of 16 or greater nt in length that is complementary to at least a portion of a gene targeted for genetic editing; and (c) an RNA aptamer that recruits methyl-CpG binding protein (MecP2);

wherein the at least one truncated gRNA, the at least one gRNA, and the aptamer comprise a single amplicon; and wherein the host cell expresses a catalytically active Cas9 nuclease.

2. The method of claim 1, wherein the Cas9 nuclease is fused to a fusion repression domain comprising Kruppel associated box (KRAB) repression domain and MecP2 (KRAB-MecP2).

3. The method of claim 1, wherein the NHEJ-associated enzyme is LigIV.

4. The method of claim 3, wherein the truncated gRNA comprises a sequence selected from the group consisting of SEQ ID NOs: 9, 10, and 11.

5. The method of claim 1, wherein the amplicon further comprises a truncated activating gRNA complementary to at least a portion of a nucleotide sequence encoding cell cycle progression factor.

6. The method of claim 5, wherein the at least one cell cycle progression factor is selected from the group consisting of hepatocyte growth factor (HGF), Cyclin A1, Cyclin A2, Cyclin B1, Cyclin E1, skp2, CtIP, cyclin dependent kinase 2 (CDK2), and Geminin (GMNN).

7. The method of claim 5, wherein the truncated activating gRNA further comprises a ligand-responsive riboswitch.

8. The method of claim 7, wherein the ligand-responsive riboswitch is a tetracycline riboswitch or theophylline riboswitch.

* * * * *

```
                            SEQUENCE LISTING

Sequence total quantity: 34
SEQ ID NO: 1            moltype = DNA  length = 15
FEATURE                 Location/Qualifiers
misc_feature            1..15
                        note = synthetic
source                  1..15
                        mol_type = other DNA
                        organism = synthetic construct
SEQUENCE: 1
ggcaaatgcc cccgc                                                            15

SEQ ID NO: 2            moltype = DNA  length = 15
FEATURE                 Location/Qualifiers
misc_feature            1..15
                        note = synthetic
source                  1..15
                        mol_type = other DNA
                        organism = synthetic construct
SEQUENCE: 2
ggcggggggca tttgc                                                           15

SEQ ID NO: 3            moltype = DNA  length = 15
FEATURE                 Location/Qualifiers
misc_feature            1..15
                        note = synthetic
source                  1..15
                        mol_type = other DNA
                        organism = synthetic construct
SEQUENCE: 3
gcggcgagca gctgg                                                            15

SEQ ID NO: 4            moltype = DNA  length = 15
FEATURE                 Location/Qualifiers
misc_feature            1..15
                        note = synthetic
source                  1..15
                        mol_type = other DNA
                        organism = synthetic construct
SEQUENCE: 4
ggctgctcgc cgcgc                                                            15

SEQ ID NO: 5            moltype = DNA  length = 15
FEATURE                 Location/Qualifiers
misc_feature            1..15
                        note = synthetic
source                  1..15
                        mol_type = other DNA
                        organism = synthetic construct
SEQUENCE: 5
ggtgtctggg acgtc                                                            15

SEQ ID NO: 6            moltype = DNA  length = 15
FEATURE                 Location/Qualifiers
misc_feature            1..15
                        note = synthetic
source                  1..15
                        mol_type = other DNA
                        organism = synthetic construct
SEQUENCE: 6
gacctgacgc ccctc                                                            15

SEQ ID NO: 7            moltype = DNA  length = 15
FEATURE                 Location/Qualifiers
misc_feature            1..15
                        note = synthetic
source                  1..15
                        mol_type = other DNA
                        organism = synthetic construct
```

```
SEQUENCE: 7
gagtctacag cgctg                                                      15

SEQ ID NO: 8              moltype = DNA  length = 15
FEATURE                   Location/Qualifiers
misc_feature              1..15
                          note = synthetic
source                    1..15
                          mol_type = other DNA
                          organism = synthetic construct
SEQUENCE: 8
gcatcaccgc tttga                                                      15

SEQ ID NO: 9              moltype = DNA  length = 15
FEATURE                   Location/Qualifiers
misc_feature              1..15
                          note = synthetic
source                    1..15
                          mol_type = other DNA
                          organism = synthetic construct
SEQUENCE: 9
gggcagccat caaag                                                      15

SEQ ID NO: 10             moltype = DNA  length = 15
FEATURE                   Location/Qualifiers
misc_feature              1..15
                          note = synthetic
source                    1..15
                          mol_type = other DNA
                          organism = synthetic construct
SEQUENCE: 10
ggacaaaaga ggtga                                                      15

SEQ ID NO: 11             moltype = DNA  length = 21
FEATURE                   Location/Qualifiers
misc_feature              1..21
                          note = synthetic
source                    1..21
                          mol_type = other DNA
                          organism = synthetic construct
SEQUENCE: 11
gtcgacgcca caccgtttat t                                               21

SEQ ID NO: 12             moltype = DNA  length = 35
FEATURE                   Location/Qualifiers
misc_feature              1..35
                          note = synthetic
source                    1..35
                          mol_type = other DNA
                          organism = synthetic construct
SEQUENCE: 12
cagcgtgtcc ggctagggat aacagggtaa tacct                                35

SEQ ID NO: 13             moltype = DNA  length = 35
FEATURE                   Location/Qualifiers
misc_feature              1..35
                          note = synthetic
source                    1..35
                          mol_type = other DNA
                          organism = synthetic construct
SEQUENCE: 13
gtcgcacagg ccgatcccta ttgtcccatt atgga                                35

SEQ ID NO: 14             moltype = DNA  length = 24
FEATURE                   Location/Qualifiers
misc_feature              1..24
                          note = synthetic
source                    1..24
                          mol_type = other DNA
                          organism = synthetic construct
SEQUENCE: 14
caccggtgtc cggctaggga taac                                            24

SEQ ID NO: 15             moltype = DNA  length = 24
FEATURE                   Location/Qualifiers
misc_feature              1..24
                          note = synthetic
```

```
source                  1..24
                        mol_type = other DNA
                        organism = synthetic construct
SEQUENCE: 15
ccacaggccg atccctattg caaa                                              24

SEQ ID NO: 16           moltype = DNA   length = 32
FEATURE                 Location/Qualifiers
misc_feature            1..32
                        note = synthetic
source                  1..32
                        mol_type = other DNA
                        organism = synthetic construct
SEQUENCE: 16
aaacaccggg tcttcgagaa gacctgtttt ag                                     32

SEQ ID NO: 17           moltype = DNA   length = 32
FEATURE                 Location/Qualifiers
misc_feature            1..32
                        note = synthetic
source                  1..32
                        mol_type = other DNA
                        organism = synthetic construct
SEQUENCE: 17
tttgtggccc agaagctctt ctggacaaaa tc                                     32

SEQ ID NO: 18           moltype = DNA   length = 34
FEATURE                 Location/Qualifiers
misc_feature            1..34
                        note = synthetic
source                  1..34
                        mol_type = other DNA
                        organism = synthetic construct
SEQUENCE: 18
aaacaccggt gtccggctag ggataacgtt ttag                                   34

SEQ ID NO: 19           moltype = DNA   length = 34
FEATURE                 Location/Qualifiers
misc_feature            1..34
                        note = synthetic
source                  1..34
                        mol_type = other DNA
                        organism = synthetic construct
SEQUENCE: 19
tttgtggcca caggccgatc cctattgcaa aatc                                   34

SEQ ID NO: 20           moltype = DNA   length = 30
FEATURE                 Location/Qualifiers
misc_feature            1..30
                        note = synthetic
source                  1..30
                        mol_type = other DNA
                        organism = synthetic construct
SEQUENCE: 20
ccaccggaga cgggataccg tctctgttta                                        30

SEQ ID NO: 21           moltype = DNA   length = 30
FEATURE                 Location/Qualifiers
misc_feature            1..30
                        note = synthetic
source                  1..30
                        mol_type = other DNA
                        organism = synthetic construct
SEQUENCE: 21
ggtggcctct gccctatggc agagacaaat                                        30

SEQ ID NO: 22           moltype = DNA   length = 24
FEATURE                 Location/Qualifiers
misc_feature            1..24
                        note = synthetic
misc_feature            6..19
                        note = n is a, c, g, or t
source                  1..24
                        mol_type = other DNA
                        organism = synthetic construct
SEQUENCE: 22
ccaccnnnnn nnnnnnnnng ttta                                              24
```

-continued

```
SEQ ID NO: 23              moltype = DNA  length = 24
FEATURE                    Location/Qualifiers
misc_feature               1..24
                           note = synthetic
misc_feature               6..19
                           note = n is a, c, g, or t
source                     1..24
                           mol_type = other DNA
                           organism = synthetic construct
SEQUENCE: 23
ggtggnnnnn nnnnnnnnnc aaat                                          24

SEQ ID NO: 24              moltype = DNA  length = 14
FEATURE                    Location/Qualifiers
misc_feature               1..14
                           note = synthetic
source                     1..14
                           mol_type = other DNA
                           organism = synthetic construct
SEQUENCE: 24
gcaaatgccc ccgc                                                     14

SEQ ID NO: 25              moltype = DNA  length = 14
FEATURE                    Location/Qualifiers
misc_feature               1..14
                           note = synthetic
source                     1..14
                           mol_type = other DNA
                           organism = synthetic construct
SEQUENCE: 25
gcgggggcat ttgc                                                     14

SEQ ID NO: 26              moltype = DNA  length = 14
FEATURE                    Location/Qualifiers
misc_feature               1..14
                           note = synthetic
source                     1..14
                           mol_type = other DNA
                           organism = synthetic construct
SEQUENCE: 26
cggcgagcag ctgg                                                     14

SEQ ID NO: 27              moltype = DNA  length = 14
FEATURE                    Location/Qualifiers
misc_feature               1..14
                           note = synthetic
source                     1..14
                           mol_type = other DNA
                           organism = synthetic construct
SEQUENCE: 27
gctgctcgcc gcgc                                                     14

SEQ ID NO: 28              moltype = DNA  length = 14
FEATURE                    Location/Qualifiers
misc_feature               1..14
                           note = synthetic
source                     1..14
                           mol_type = other DNA
                           organism = synthetic construct
SEQUENCE: 28
gtgtctggga cgtc                                                     14

SEQ ID NO: 29              moltype = DNA  length = 14
FEATURE                    Location/Qualifiers
misc_feature               1..14
                           note = synthetic
source                     1..14
                           mol_type = other DNA
                           organism = synthetic construct
SEQUENCE: 29
acctgacgcc cctc                                                     14

SEQ ID NO: 30              moltype = DNA  length = 14
FEATURE                    Location/Qualifiers
misc_feature               1..14
                           note = synthetic
source                     1..14
                           mol_type = other DNA
                           organism = synthetic construct
```

```
SEQUENCE: 30
agtctacagc gctg                                                                    14

SEQ ID NO: 31           moltype = DNA  length = 14
FEATURE                 Location/Qualifiers
misc_feature            1..14
                        note = synthetic
source                  1..14
                        mol_type = other DNA
                        organism = synthetic construct
SEQUENCE: 31
catcaccgct ttga                                                                    14

SEQ ID NO: 32           moltype = DNA  length = 14
FEATURE                 Location/Qualifiers
misc_feature            1..14
                        note = synthetic
source                  1..14
                        mol_type = other DNA
                        organism = synthetic construct
SEQUENCE: 32
ggcagccatc aaag                                                                    14

SEQ ID NO: 33           moltype = DNA  length = 14
FEATURE                 Location/Qualifiers
misc_feature            1..14
                        note = synthetic
source                  1..14
                        mol_type = other DNA
                        organism = synthetic construct
SEQUENCE: 33
gacaaaagag gtga                                                                    14

SEQ ID NO: 34           moltype = DNA  length = 20
FEATURE                 Location/Qualifiers
misc_feature            1..20
                        note = synthetic
source                  1..20
                        mol_type = other DNA
                        organism = synthetic construct
SEQUENCE: 34
tcgacgccac accgtttatt                                                              20
```